US006362205B2

United States Patent
Hansen et al.

(10) Patent No.: US 6,362,205 B2
(45) Date of Patent: Mar. 26, 2002

(54) SUBSTITUTED 3,3-DIAMINO-2-PROPENENITRILES, THEIR PREPARATION AND USE

(75) Inventors: John Bondo Hansen, Jyderup; Tina Moller Tagmose, Ballerup; John Patrick Mogensen, Vanlose; Florencio Zaragoza Dorwald, Ballerup; Anker Steen Jorgensen, Copenhagen O, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/809,952

(22) Filed: Mar. 16, 2001

Related U.S. Application Data

(63) Continuation of application No. 09/433,264, filed on Nov. 4, 1999, now abandoned.
(60) Provisional application No. 60/108,728, filed on Nov. 17, 1998.

(30) Foreign Application Priority Data

Nov. 5, 1998 (DK) .......................... 1998 01427

(51) Int. Cl.$^7$ ..................... C07C 255/07; A61K 31/277
(52) U.S. Cl. ................... 514/352; 514/367; 514/407; 514/466; 514/523; 546/312; 548/178; 548/371.7; 549/439; 558/391; 558/395
(58) Field of Search ............... 558/391, 395; 546/312; 549/439; 548/371.7, 178; 514/523, 352, 466, 407, 367

(56) References Cited

U.S. PATENT DOCUMENTS 5,955,548 A * 9/1999 Dorwald et al. .......... 525/329.4

FOREIGN PATENT DOCUMENTS

| EP | 0 413 343 | 2/1991 |
| EP | 0 760 362 | 3/1997 |
| WO | WO 98/50344 | 11/1998 |

OTHER PUBLICATIONS

W.–D. Rudorf, Tetrahedron, vol. 36, pp. 1791–1799 (1980).

Abstract of article by Augustin et al., Synthesis and reactivity of phenylsulfonylcyanoketene–S, S–acetals (1977).

* cited by examiner

*Primary Examiner*—Laura L. Stockton
(74) *Attorney, Agent, or Firm*—Reza Green, Esq.; Peter J. Waibel, Esq.

(57) ABSTRACT

Described are substituted cyanoenamines of formula I

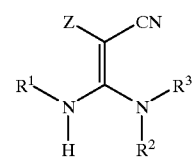

wherein Z, $R^1$, $R^2$ and $R^3$ are defined in the description, compositions thereof and methods for preparing these compounds. These compounds are useful in the treatment of diseases of the central nervous system, the cardiovascular system, the pulmonary system, the gastrointestinal system and the endocrinologic system.

6 Claims, No Drawings

SUBSTITUTED 3,3-DIAMINO-2-PROPENENITRILES, THEIR PREPARATION AND USE

CROSS-REFERENCE TO RELATED APPLICATIONS

This application is a continuation of Ser. No. 09/433,264 filed Nov. 4, 1999 now abandoned, and claims priority under 35 U.S.C. 119 of U.S. provisional application No. 60/108,728 filed on Nov. 17, 1998, and Danish application PA 1998 01427 filed on Nov. 5, 1998, the contents of which are fully incorporated herein by reference.

FIELD OF THE INVENTION

The present invention relates to substituted 3,3-diamino-2-propenenitriles, in the following also referred to as cyanoenamines, to methods for their preparation, to compositions comprising the compounds, to the use of these compounds as medicaments and their use in therapy e.g. in the treatment of diseases of the central nervous system, the cardiovascular system, the pulmonary system, the gastrointestinal system and the endocrinologic system.

Optionally, the pharmaceutical composition of the invention may comprise a compound of formula I combined with one or more other pharmacologically active compounds, e.g. an antidiabetic or other pharmacologically active material, including compounds for the treatment and/or prophylaxis of insulin resistance and diseases wherein insulin resistance is the pathophysiological mechanism. Suitable antidiabetics comprise insulin as well as orally active hypoglycemic agents such as sulphonylureas, e.g. glibenclamide and glipizide; biguanides, e.g. metformin; benzoic acid derivatives, e.g. repaglinide; and thiazolidinediones, e.g. troglitazone and ciglitazone.

BACKGROUND OF THE INVENTION

Potassium channels play an important role in membrane potential. Among the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic-cells, skeletal muscles, smooth muscles, central neurones and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulfonylureas which have been used for the treatment of non-insulin-dependent diabetes mellitus act by stimulating insulin release through an inhibition of the $K_{ATP}$-channels on pancreatic beta-cells. The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hair growth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labor.

Since some $K_{ATP}$-openers are able to antagonize vasospasms in basilar or cerebral arteries the compounds of the present invention can be used for the treatment of vasospastic disorders such as subarachnoid hemorrhage and migraine.

Potassium channel openers hyperpolarizes neurons and inhibit neurotransmitter release and it is expected that the present compounds can be used for the treatment of various diseases of the central nervous system, e.g. epilepsia, ischemia and neurodegenerative diseases, and for the management of pain.

Recently, it has been shown that diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. *Biochem. Pharmacol,* 47, 1381–1386 (1994); Pirotte B. et al., *J. Med. Chem.,* 36, 3211–3213 (1993). Diazoxide has furthermore been shown to delay the onset of diabetes in BB-rats (Vlahos W D et al. *Metabolism* 40, 39–46 (1991)). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that such potassium channel openers can be used for treatment of diseases characterized by an overproduction of insulin and for the treatment and prevention of diabetes.

DESCRIPTION OF THE INVENTION

The present invention relates to substituted 3,3-diamino-2-propenenitriles, in the following also referred to as cyanoenamines, of the general formula I:

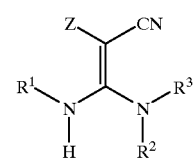

wherein $R^1$ is alkyl optionally substituted with halogen, hydroxy, alkoxy, aryloxy, alkylthio, arylthio, dialkylamino, arylalkylamino or diarylamino; or aralkyl optionally substituted with alkyl, trifluoromethyl, aryl, a 5-,6- or 7-membered heterocyclic system, halogen, alkoxy, methylenedioxo, aryloxy, dialkylamino, alkylarylamino, diarylamino, nitro, alkylsulfonyl, arylsulfonyl, cyano, alkoxycarbonyl or aminocarbonyl; or aryl optionally substituted with alkyl, trifluoromethyl, aryl, a 5-,6- or 7-membered heterocyclic system, halogen, alkoxy, methylenedioxo, aryloxy, dialkylamino, alkylarylamino, diaryl-amino, nitro, alkylsulfonyl, arylsulfonyl, cyano, alkoxycarbonyl or aminocarbonyl; or a 5-,6- or 7-membered heterocyclic system optionally substituted with alkyl, aryl, a 5-,6- or 7-membered heterocyclic system, halogen, alkoxy, aryloxy, dialkylamino, alkylarylamino, diarylamino, nitro, alkylsulfonyl, arylsulfonyl, cyano, alkoxycarbonyl or aminocarbonyl;

$R^2$ and $R^3$ are independently hydrogen, alkyl optionally substituted with aryl, a 5-,6- or 7-membered heterocyclic system, halogen, hydroxy, alkoxy, aryloxy, alkylthio, arylthio, dialkylamino, arylalkylamino or diarylamino; aryl, optionally substituted with alkyl, aryl, a 5-,6- or 7-membered heterocyclic system, halogen, trifluoromethyl, alkoxy, aryloxy, dialkylamino, alkylarylamino, diarylamino, nitro, alkylsulfonyl, arylsulfonyl, cyano, alkoxycarbonyl or aminocarbonyl; a 5-,6- or 7-membered heterocyclic system optionally substituted with alkyl, aryl, a 5-,6- or 7-membered heterocyclic system, halogen, alkoxy, aryloxy, dialkylamino, alkylarylamino, diarylamino, nitro, alkylsulfonyl, arylsulfonyl, cyano, alkoxycarbonyl or aminocarbonyl;

or $R^2$ and $R^3$ are linked together by —$(CH_2)_n$—, n being 4–7, provided that $R^2$ and $R^3$ cannot be hydrogen at the same time;

Z is hydrogen, cyano, carbonylalkyl, alkoxycarbonyl, optionally substituted aminocarbonyl, alkylsulfonyl or arylsulfonyl optionally substituted with alkyl, aryl, a 5-,6- or 7-membered heterocyclic system, halogen, alkoxy, aryloxy, dialkylamino, alkylarylamino, diarylamino, nitro, alkylsulfonyl, arylsulfonyl, cyano, alkoxycarbonyl or aminocarbonyl; or arylsulfonyl optionally substituted with alkyl, aryl, a 5-,6- or 7-membered heterocyclic system, halogen, alkoxy, aryloxy, dialkylamino, alkylarylamino, diarylamino, nitro, alkylsulfonyl, arylsulfonyl, cyano, alkoxycarbonyl or aminocarbonyl;

or pharmaceutically acceptable salts thereof.

Within its scope the invention includes all diastereomers and enantiomers of compounds of formula I, some of which are optically active, and also their mixtures including racemic mixture thereof.

The scope of the invention also includes all tautomeric forms of the compounds of formula I as well as metabolites or prodrugs.

In a preferred embodiment of the invention, Z is alkylsulfonyl or arylsulfonyl substituted with halogen. More preferred, Z is methylsulfonyl, isopropylsulfonyl or 4-chlorophenylsulfonyl.

In a further preferred embodiment of the invention, $R^1$ is optionally substituted aryl. More preferred optionally substituted phenyl and most preferred phenyl substituted by one or two perhalomethyl groups, one or two alkoxy groups, one or two halogen groups or one or two cyano groups.

A preferred perhalomethyl group is trifluoromethyl.

The most preferred phenyl substituents are 3,5-dichloro or 3,5-dialkoxy substituents.

In a further preferred embodiment of the invention, $R^2$ is cyclic alkyl with from 3 to 5 carbon atoms in the ring, most preferred is cyclobutyl.

In another preferred embodiment of the invention, $R^2$ is 1,1-dimethylpropyl.

A "metabolite" of a compound disclosed in this application is an active derivative of a compound disclosed herein which is produced when the compound is metabolized. Metabolites of compounds disclosed herein can be identified either by administration of a compound to a host and an analysis of blood samples from the host, or by incubation of compounds with hepatic cells in vitro and analysis of the incubant. A "prodrug" is a compound that either is converted into a compound disclosed in the application in vivo or has the same active metabolite as a compound disclosed in this application.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methane-sulfonic, ethane sulfonic, picric and the like, and include acids related to the pharmaceutically acceptable salts listed in *Journal of Pharmaceutical Science*, 66, 2 (1977) and incorporated herein by reference, or lithium, sodium, potassium, magnesium and the like.

The term "5-,6- or 7-membered heterocyclic system" as used herein refers to: a monocyclic unsaturated or saturated system containing one, two or three hetero atoms selected from nitrogen, oxygen and sulfur and having 5 members, e.g. pyrrole, furan, thiophene, pyrroline, dihydrofuran, dihydrothiophene, imidazole, imidazoline, pyrazole, pyrazoline, oxazole, thiazole, isoxazole, isothiazole, 1,2,3-oxadiazole, furazan, 1,2,3-triazole, 1,2,3-thiadiazole or 2,1,3-thiadiazole; an aromatic monocyclic system containing two or more nitrogen atoms and having 6 members, e.g. pyrazine, pyrimidine, pyridazine, 1,2,4-triazine, 1,2,3-triazine or tetrazine; a non-aromatic monocyclic system containing one or more hetero atoms selected from nitrogen, oxygen and sulfur and having 6 or 7 members, e.g. pyran, thiopyran, piperidine, dioxane, oxazine, isoxazine, dithiane, oxathine, thiazine, piperazine, thiadiazine, dithiazine, oxadiazine or oxoazepane.

Alkyl refers to lower straight, cyclic, bicyclic, fused or branched alkyl having 1 to 15 carbon atoms, preferentially 1 to 6 carbon atoms. Aryl refers to phenyl or phenyl substituted with alkyl or phenyl, or phenyl fused with cycloalkyl, or polycyclic aromatic systems such as naphthyl, anthracenyl, phenanthrenyl, fluorenyl, etc. Alkylene refers to lower straight, cyclic, fused or branched alkylene having 1 to 15 carbon atoms, preferentially 1 to 6 carbon atoms. Alkoxy refers to —O-alkyl and aryloxy refers to —O-aryl. Cyano refers to —CN, hydroxy refers to —OH, amino refers to —$NH_2$ and nitro refers to —$NO_2$. Dialkylamino refers to —N(alkyl)$_2$. Alkylarylamino refers to —N(alkyl)(aryl) and diarylamino refers to —N(aryl)$_2$. Halogen refers to —F, —Cl, —Br and —I. Aralkyl refers to -alkylene-aryl. Alkylthio refers to —S-alkyl and arylthio refers to —S-aryl. Alkoxycarbonyl refers to —CO—O-alkyl and aminocarbonyl refers to —CO—N(alkyl)$_2$, —CO—N(alkyl)(aryl) or —CO—N(aryl)$_2$. Carbonylalkyl refers to —CO-alkyl. A leaving group refers to a group or atom capable of existing in solution as a negatively charged species, or a positively charged group or atom.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinologic system.

The compounds of the present invention may also be used for the treatment of diseases associated with decreased skeletal muscle blood flow such as Reynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the ureter. Potassium channel openers also relax urinary bladder smooth muscle, thus, the compounds of the present invention can be used for the treatment of urinary incontinence.

The present compounds could also be used for treatment of conditions associated with disturbances in gastrointestinal mobility such as irritable bowel syndrome. Additionally these compounds can be used for the treatment of premature labor and dysmenorrhea.

Further, potassium channel openers promote hairgrowth, therefore, the compounds of the present invention can be used for the treatment of baldness.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of noninsulin dependent diabetes (NIDDM). It is expected that potassium channel openers and hence the compounds of the present invention can be used for counteracting the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

In early cases of insulin dependent diabetes (IDDM) or in prediabetic cases, potassium channel openers and hence the present compounds can be used to induce betacell rest which may prevent the progression of the autoimmune disease.

Compounds of the present invention which act as blockers of $K_{ATP}$-channels can be used for the treatment of NIDDM.

Preferably, the compounds of the present invention may be used for treatment or prevention of diseases of the endocrinologic system such as hyperinsulinemia and diabetes.

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinemia and treatment or prevention of diabetes.

Furthermore, the invention also relates to the use of the inventive compounds of formula I as medicaments useful for treating hyperinsulinemia and treating or preventing diabetes.

In yet another aspect, the present invention relates to a method of preparing compounds of the invention.

The method comprises synthesis of cyanoenamines by the following reaction scheme:

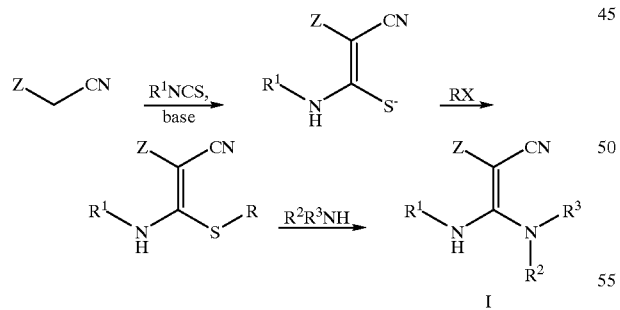

Acceptor substituted acetonitriles were reacted with isothiocyanates in the presence of a base. The resulting salts of the adducts were treated with alkyl halide to give the corresponding alkylsulfanyl propenenitriles, which were reacted with primary and secondary amines to give cyanoenamines of formula I.

PRIOR ART

Some derivatives of 2-cyano-3-(dimethylamino)-3-arylamino-2-propenenitriles have been claimed to be angio-tensin II antagonists (EP 591891, Chem. Abstr. 1995, 122, 81364; Chem. Abstr. 1994, 121, 300890). Example:

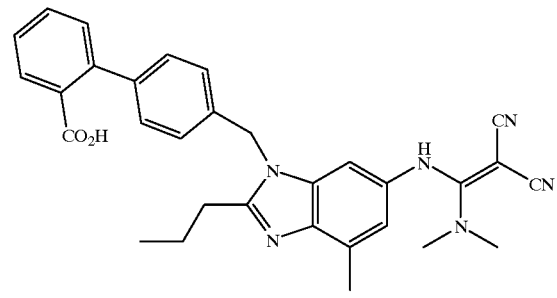

Other compounds containing this substructural element have been claimed to be antithrombotics (EP 547517, Chem. Abstr. 1993, 119, 249845; Chem. Abstr. 1993, 119, 180666), e.g.:

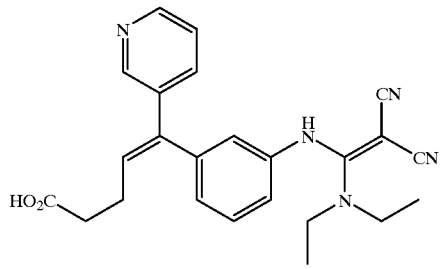

Several 3-(arylamino)-3-(alkylamino)-2-cyano-2-propenenitriles and -2-acrylamides have been claimed as fungicides and herbicides (EP 10396, Chem. Abstr. 1982, 97, 140276; Chem. Abstr. 1980, 93, 144701), some examples being:

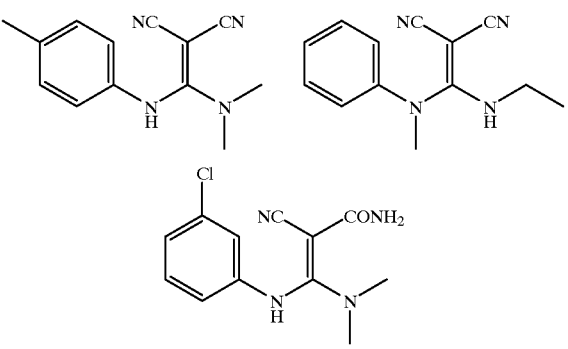

The reaction of amines RR'NH with mono-imidates of malononitrile of the general formula NC—CH$_2$—C(OR)=NH give compounds of the type RR'N—C(NH$_2$)=CH—CN, where one of the two amino groups is limited to be NH$_2$ (Cocco, M. T.; Congiu, C.; Maccioni, A.; Plumitallo, A., *J. Heterocycl. Chem.*, 1989, 26,1859–1862; Klemm, K.; Pruesse, W.; Baron, L.; Daltrozzo, E., *Chem. Ber.*, 1981, 114, 2001–2018; Cocco, M. T.; Onnis, V., *Synthesis*, 1993, 2, 199–201; Fanshawe, W. J. et al., *J. Org. Chem.*, 1964, 29, 308–311; Troschuetz, R.; Dennstedt, T., *Arch. Pharm. (Weinheim Ger.)*, 1994, 327, 85–90).

A further method consists in the reaction of O-alkylated cyanoacetamides with aliphatic amines (G. J. Durant et al., patent, CH 606026, *Chem. Abstr.* 1979, 90, 87449, G. J. Durant, U.S. Pat. No. 4,024,260, *Chem. Abstr.,* 1977, 87, 135327). Also the reaction of 3,3-dimethoxyacrylonitrile with amines, which can be carried out stepwise in order to prepare compounds of the general formula RR'N—C(NR"R'")=CH—CN, has been reported (G. J. Durant, U.S. Pat. No. 4,277,485, *Chem. Abstr.,* 1981, 95, 156591) and used for the preparation of ranitidine-analogues.

Moreover, the reaction of 3,3-dichloroacrylonitrile with amines has been reported to give cyanoenamines of the general structure (RR'N)$_2$C=CH—CN, with two identical amine-moieties RR'N— (Hashimoto et al., *J. Org. Chem.,* 1970, 35, 828–831; Takeda Chem.Ind.Ltd., JP 7022328, 1970, *Chem.Abstr.,* 73, 98434z). In addition to these, some special methods for the synthesis of these compounds have been described (e.g. Sasaki, T.; Kojima, A. *J. Chem. Soc. Sec. C,* 1970, 476–480; Clark, J., Parvizi, B., Southon, I. W., *J. Chem. Soc., Perkin Trans.* 1, 1976, 125–130; Smith; Kline and French Lab. Lim, FR 2229417, DE 2423813, *Chem. Abstr.,* 82, 170943; Meyer; K., *Justus Liebigs Ann. Chem.,* 1978, 1491; Elagamey, A. G. A.; El-Taweel, F. M. A., *J. Prakt. Chem.,* 1991, 333, 333–338).

For the preparation of 2-acceptor-substituted 3,3-bis(alkyl/arylamino)-2-propenenitriles, several different synthetic methods have been described (Elvidge, J. A. et al., *J. Chem. Soc., Perkin Trans. I,* 1983, 1741–1744; Yatsishin, A. A.. et al., *Zh. Org. Khim.* 1979, 15, 1381–1384; Hartke, K., *Angew. Chem.* 1964, 76, 781)

Pharmacological Methods

The ability of the compounds to interact with potassium channels can be determined by various methods. When patch-clamp techniques (Hamill O. P., Marty A., Nefer E., Sakman B. and Sigworth F. J., *Plügers Arch.* 1981, 391, 85–100) are used the ionic current through a single channel of a cell can be recorded.

The activity of the compounds as potassium channel openers can also be measured as relaxation of rat aortas rings according to the following procedure:

A section of rat thoracic aorta between the aortic arch and the diaphragm was dissected out and mounted as ring preparations as described by Taylor P. D. et al. , *Brit. J. Pharmacol.,* 1994, 111, 42–48.

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

In the pancreatic beta-cell the opening of the $K_{ATP}$-channels can be determined by measuring the subsequent change in the concentration of cytoplasmic free $Ca^{2+}$ concentration according to the method of Arkhammer P. et al. , *J. Biol. Chem.* 1987, 262, 5448–5454.

$^{86}Rb^+$ Efflux from a β-cell Line

The RIN 5F cell line was grown in RPMI 1640 with Glutamax I, supplemented with 10% fetal calf serum (from GibcoBRL, Scotland, UK) and maintained in an atmosphere of 5% $CO_2$/95% air at 37° C. The cells were detached with a Trypsin-EDTA solution (from GibcoBRL, Scotland, UK), resuspended in medium, added 1 mCi/mL $^{86}Rb^+$ and replated into microtiter plates (96 well cluster 3596, sterile, from Costar Corporation, MA, USA) at a density of 50000 cells/well in 100 µl/well, and grown 24 hours before use in assay.

The plates were washed 4 times with Ringer buffer (150 mM NaCl, 10 mM Hepes, 3.0 mM KCl, 1.0 mM $CaCl_2$, 20 mM sucrose, pH 7.1). Eighty µL Ringer buffer and 1 µL control- or test compound dissolved in DMSO was added. After incubation 1 h at room temperature with a lid, 50 µL of the supernatant was transferred to PicoPlates (Packard Instrument Company, CT, USA) and 100 µL MicroScint40 (Packard Instrument Company, CT, USA) added. The plates were counted in TopCount (Packard Instrument Company, CT, USA) for 1 min/well at the $^{32}P$ program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}$=c and $EM_{max}$=d, when the curve is turned of at infinite concentrations.

In addition the effect of $K_{ATP}$-channel modulators on pancreatic beta-cells can be determined by measuring the increase or decrease in insulin release from insulin producing beta-cell lines or isolated islets.

Effect of $K_{ATP}$-channel modulators can be measured using the following procedure: The beta cells are cultured with change of media every three-four days.

Cells are then seeded in 96 well microtiter dishes and cultured for three day at 38° C., 5% $CO_2$ and 95% humidity.

The cells are washed with NN -buffer (+10 mM Hepes+ 0.1% BSA) for one minute and glucose (final conc. 22 mM), IBMX (final conc.0.1 mM) and compounds (final conc. from $5×10^{-5}$ M–$5×10^{-8}$ M) added. All cells are then incubated for three hours (38° C., 5% $CO_2$ and 95% humidity).

Supernates are harvested into Greiner minisorb microtiter wells and frozen. Insulin is measured using elisa-techniques.

The compounds of the present invention shows high selectivity of the insulin release test compared to the relaxation of rat aorta rings test.

The compounds according to the invention are effective over a wide dosage range. In general satisfactory results are obtained with dosages from about 0.05 mg to about 1000 mg, preferably from about 0.1 mg to about 500 mg, per day. A most preferable dosage is about 5 mg to about 200 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

Due to their high degree of activity, the compounds of the invention may be administered to a mammal, especially a human, in need of such treatment, prevention, elimination, alleviation or amelioration of various diseases as mentioned above and especially of diseases of the endocrinologic system such as hyperinsulinemia and diabetes. Such mammals include also animals, both domestic animals, e.g. household pets, and non-domestic animals such as wildlife.

EXAMPLES

The process of preparing the compounds of formula I is further illustrated in the following examples which, however, are not to be construed as limiting.

Example 1

3-[3,5-bis(tifluoromethyl)phenylamino]-2-(4-chlorophenylsulfonyl)-3-(1,2,2-trimethylpropylamino)-2-propenenitrile 1) 3-(3,5-Bis(trifluoromethyl)phenylamino)-2-(4-chlorophenylsulfonyl)-3-methylsulfanyl-2-propenenitrile To a solution of 4-chlorophenylsulfonylacetonitrile (1.10 g, 5.10 mmol) in dry acetone (12 ml) first dry potassium carbonate (1.41 g, 10.2 mmol) and then 3,5-bis (trifluoromethyl)phenyl isothiocyanate (1,44 g, 5.31 mmol) were added. The resulting mixture was stirred at room temperature under nitrogen for 1 h, and then filtered. To the filtrate a solution of sodium hydrogencarbonate (0.86 g) in water (15 ml) and methyl iodide (0.945 ml, 15.3 mmol) was added. The mixture was stirred at room temperature for 3.5 h. Then pH was adjusted to ~4 with 1N HCl. The precipitate was filtered off and washed with water to give 2.39 g (93%) of the title compound. Recrystallisation could be done from ethyl acetate/heptane 1:3. Mp 150.5–152.5° C. $^1$H NMR (300 MHz, CDCl$_3$): δ=2.25 (s, 3H), 7.57 (d, 2H), 7.79 (s, 2H), 7.83 (s, 1H), 7.88 (d, 2H), 10.0 (br s, 1H); MA calc for $C_{18}H_{11}ClF_6N_2O_2S_2$: C, 43.17%; H, 2.21%; N, 5.59%. Found: C, 43.25%; H, 2.16%; N, 5.59%.

2) 3-[3,5-Bis(trifluoromethyl)phenylamino]-2-(4-chlorophenylsulfonyl)-3-(1,2,2-trimethylpropylamino)-2-propenenitrile 3-(3,5-Bis(trifluoromethyl)phenylamino)-2-(4-chlorophenylsulfonyl)-3-methylsulfanyl-2-propenenitrile (0.300 g, 0.6 mmol) was stirred in 1,2,2-trimethylpropylamine (1 ml) for 19 h at 75° C. under nitrogen. The reaction mixture was concentrated and the residue dissolved in DCM, washed twice with 1N aqueous HCl and once with water. The organic phase was dried (sodium sulfate) and concentrated. The residue was crystallised from ethyl acetate/heptane 1:3 to give 225 mg (68%) of the title compound. Mp 155.5–158.5° C. $^1$H NMR (300 MHz, CDCl$_3$): δ=0.9 (s, 9H), 1.0 (d, 3H), 3.0 (m, 1H), 7.40 (s, 2H), 7.50 (d, 2H), 7.70 (s, 1H), 7.82 (d, 2H); MA calc for $C_{23}H_{22}ClF_6N_3O_2S$: C, 49.87%; H, 4.00%; N, 7.59%. Found: C, 49.86%; H, 4.29%, N, 7.55%.

Example 2

3-[3,5-Bis(trifluoromethyl)phenylamino]-2-(4-chlorophenylsulfonyl)-3-cyclopentylamino-2-propenenitrile 3-(3,5-Bis(trifluoromethyl)phenylamino)-2-(4-chlorophenylsulfonyl)-3-methylsulfanyl-2-propenenitrile (0.400 g, 0.8 mmol) was stirred in cyclopentylamine (2 ml) at 80° C. for 2 h and at room temperature for 16 h under nitrogen. Work up as desciped in Example 1, 2) gave 305 mg (71%) of the title compound as pale yellow crystals. Mp 199–200° C. $^1$H NMR (300 MHz, CDCl$_3$): δ=1.4–1.65 (m, 4H), 1.65–1.85 (m, 4H), 3.56 (sextet, 1H), 7.42 (s, 2H), 7.49 (d, 2H), 7.67 (s, 1 H), 7.78 (d, 2H); MA calc for $C_{22}H_{18}ClF_6N_3O_2S$: C, 49.12%; H, 3.37%; N, 7.18%. Found: C, 48.93%; H, 3.31%; N, 7.58%.

Example 3

3-[3,5-Bis(trifluoromethyl)phenylamino]-2-(4-chlorophenylsulfonyl)-3-isopropylamino-2-propenenitrile 3-(3,5-Bis(trifluoromethyl)phenylamino)-2-(4-chlorophenylsulfonyl)-3-methylsulfanyl-2-propenenitrile (0.400 g, 0.8 mmol) was stirred in isopropylamine (2 ml) at 80° C. in a sealed flask for 20 h. Work up as described in Example 1, 2) gave 254 mg (62%) of the title compound as white crystals. Mp 197–198.5° C. $^1$H NMR (300 MHz, CDCl$_3$): δ=1.5 (d, 6H), 3.37 (m, 1H), 7.42 (s, 2H), 7.48 (d, 2H), 7.67 (s, 1H), 7.79 (d, 2H); MA calc for $C_{20}H_{16}ClF_6N_3O_2S$: C, 46.93%; H, 3.15%; N, 8.21%. Found: C, 47.16%; H, 3.14%; N, 8.10%.

Example 4

3-[3,5-Bis(trifluoromethyl)phenylamino]-2-(4-chlorophenylsulfonyl)-3-cyclobutylamino-2-propenenitrile 3-(3,5-Bis(trifluoromethyl)phenylamino)-2-(4-chlorophenylsulfonyl)-3-methylsulfanyl-2-propenenitrile (0.400 g, 0.8 mmol) was stirred in cyclobutylamine (0.70 ml) at 60° C. for 20 h. Work up as described in Example 1, 2) gave 354 mg (85%) of the title compound as white crystals. Mp 190.5–193° C. $^1$H NMR (300 MHz, CDCl$_3$): δ=1.5 (m, 2H), 1.72 (m, 1H), 2.0 (m, 3H), 3.63 (sextet, 1H), 7.42 (s, 2H), 7.48 (d, 2H), 7.67 (s, 1H), 7.79 (d, 2H); MA calc for C$_{21}$H$_{16}$ClF$_6$N$_3$O$_2$S: C, 48.15%; H, 3.08%; N, 8.02%. Found: C, 48.38%; H, 3.09%; N, 7.96%.

Example 5

3-[3,5-Bis(trifluoromethyl)phenylamino]-2-(4-chlorophenylsulfonyl)-3-propylamino-2-propenenitrile 3-(3,5-Bis(trifluoromethyl)phenylamino)-2-(4-chlorophenyisulfonyl)-3-methylsulfanyl-2-propenenitrile (0.400 g, 0.8 mmol) was stirred in n-propylamine (1.0 ml) at 75° C. in a sealed flask for 19 h. Work up as described in Example 1, 2) gave 266 mg (65%) of the title compound as white crystals. Mp 196.5–198.5° C. $^1$H NMR (300 MHz, CDCl$_3$): δ=0.9 (t, 3H), 1.55 (p, 2H), 2.88 (q, 2H), 7.40 (s, 2H), 7.48 (d, 2H), 7.68 (s, 1H), 7.81 (d, 2H); MA calc for C$_{20}$H$_{16}$ClF$_6$N$_3$O$_2$S: C, 46.93%; H, 3.15%; N, 8.21%. Found: C, 46.82%; H, 3.19%; N, 8.10%.

Example 6

2-(4-Chlorophenylsulfonyl)-3-(pyrdin-3-ylamino)-3-(1,2,2-trimethylpropylamino)-2-propenenitrile 1) 2-(4-Chlorophenylsulfonyl)-3-methylsulfanyl-3-(pyridin-3-ylamino)-2-propenenitrile To a solution of 4-chlorophenylsulfonylacetonitrile (1.00 g, 4.6 mmol) in dry acetone (10 ml) first dry potassium carbonate (1.28 g, 9.3 mmol) and then pyridin-3-yl isothiocyanate (0.663 g, 4.9 mmol) were added. The resulting mixture was stirred at room temperature under nitrogen for 4 h, and then filtered. To the filtrate methyl iodide (0.315 ml, 5.1 mmol) was added. The mixture was stirred at room temperature for 16 h. The reaction mixture was concentrated and the residue was taken up into ethyl acetate and water. The organic layer was washed with 1N aqueous HCl (2×). The organic phase was dried (sodium sulfate) and concentrated. The residue was purified by flash chromatography using heptane/ethyl acetate 1:2 as eluent and recrystallisation in ethyl acetate to give 294 mg (16%) of the title compound. Mp 181–182° C. $^1$H NMR (300 MHz, CDCl$_3$): δ=2.20 (s, 3H), 7.36 (dd, 1H), 7.54 (dm, 2H), 7.6 (m, 1H), 7.88 (dm, 2H), 8.55 (m, 2H), 9.85 (br s, 1H); EI SP/MS: 365 (M+).

2) 2-(4-Chlorophenylsulfonyl)-3-(pyridin-3-ylamino)-3-(1,2,2-trimethylpropylamino)-2-propenenitrile 2-(4-Chloro-phenylsulfonyl)-3-methylsulfanyl-3-(pyridin-3-ylamino)-2-propenenitrile (0.186 g, 0.5 mmol) was stirred in 1,2,2-trimethylpropylamine (1 ml) for 22 h at 100° C. under nitrogen. The reaction mixture was concentrated. The residue was dissolved in DCM, washed with water, dried (sodium sulfate) and concentrated. The crude product was purified by flash chromatography using ethyl acetate as eluent to give 124 mg (58%) of the title compound as a syrup, which could be crystallised from ethyl acetate/heptane 2:1 to give 65 mg (30%). Mp 172–174° C. $^1$H NMR (300 MHz, CDCl$_3$): δ=0.85 (s, 9H), 0.9 (d, 3H), 3.03 (m, 1H), 7.35 (m, 2H), 7.48 (d, 2H), 7.80 (d, 2H), 8.33 (br s, 1H), 8.5 (br s, 1H).

Example 7

2-(4-Chlorophenylsulfonyl)-3-(3,5-dichlorophenylamino)-3-(1,2,2-trimethylpropylamino)-2-propenenitrile 1) 2-(4-Chlorophenylsulfonyl)-3-(3,5-dichlorophenylamino)-3-methylsulfanyl-2-propenenitrile To a solution of 4-chlorophenylsulfonylacetonitrile (1.00 g, 4.6 mmol) in dry acetone (10 ml) first dry potassium carbonate (1.28 g, 9.3 mmol) and then 3,5-dichlorophenyl isothiocyanate (0.99 g, 4.9 mmol) were added. The resulting mixture was stirred at room temperature under nitrogen for 4 h, and then filtered. To the filtrate methyl iodide (0.86 ml, 13.9 mmol) was added. The mixture was stirred at room temperature for 45 min. Then pH was adjusted to 1 with 1N aqueous HCl. The precipitate was filtered off and washed with water to give 1.86 g (93%) of a crude product. Recrystallisation from ethyl acetate/heptane (1:1) gave 1.42 g (72%) of the title compound contaminated with 4-chlorophenylsulfonylacetonitrile. Mp 128–131° C. $^1$H NMR (200 MHz, CDCl$_3$): δ=2.25 (s, 3H), 7.20 (d, 2H), 7.30 (t, 1H), 7.55 (d, 2H), 7.85 (d, 2H), 9.80 (br s, 1H); EI SP/MS: 434 (M+), 436 (M+2).

2) 2-(4-Chlorophenylsulfonyl)-3-(3,5-dichlorophenylamino)-3-(1,2, 2trimethylpropylamino)-2-propenenitrile 2-(4-Chloro-phenylsulfonyl)-3-(3,5-dichlorophenylamino)-3-methylsulfanyl-2-propenenitrile (0.347 g, 0.8 mmol) was stirred in 1,2,2-trimethylpropylamine (1 ml) for 22 h at 100° C. under nitrogen in a sealed flask. Work up as described in Example 1, 2) gave 235 mg (60%) of the title compound. Mp 163–169° C. $^1$H NMR (200 MHz, CDCl$_3$): δ=0.9 (s, 9H), 1.0 (d, 3H), 3.05 (m, 1H), 6.85 (br s, 2H), 7.2 (br s, 1H), 7.50 (d, 2H), 7.78 (d, 2H); EI SP/MS: 485 (M+), 487 (M+2), 489 (M+4), 491 (M+6).

Example 8

3-(Benzo[1,3]dioxol-5-ylamino)-2-(4-chlorophenylsulfonyl)-3-(1,2,2-trimethyl-propylamino)-2-propenenitrile 1) 3-(Benzo[1,3]dioxol-5-ylamino)-2-(4-chlorophenylsulfonyl)-3-methylsulfanyl-2-propenenitrile To a solution of 4-chlorophenylsulfonylacetonitrile (1.00 g, 4.64 mmol) in dry acetone (10 ml) first dry potassium carbonate (1.28 g, 9.3 mmol) and then 3,4-methylenedioxyphenyl isothiocyanate (0.87 g, 4.9 mmol) were added. The resulting mixture was stirred at room temperature under nitrogen for 4 h, and then filtered. To the filtrate methyl iodide (0.86 ml, 13.9 mmol) was added. The mixture was stirred at room temperature for 50 min. Then pH was adjusted to 1 with 1N aqueous HCl. The precipitate was filtered off and washed with water to give 1.12 g (59%) of the title compound. Mp 196–200° C. $^1$H NMR (200 MHz, CDCl$_3$): δ=2.22 (s, 3H), 6.05 (s, 2H), 6.68 (m, 2H), 6.80 (d, 1H), 7.53 (d, 2H), 7.87 (d, 2H), 9.80 (br s, 1H); EI SP/MS: 408 (M+).

2) 3-(Benzo[1,3]dioxol-5-ylamino)-2-(4-chlorophenylsulfonyl)-3-(1,2,2-trimethyl-propylamino)-2-propenenitrile 3-(Benzo[1,3]dioxol-5-ylamino-2-(4-chlorophenylsulfonyl)-3-methylsulfanyl-2-propenenitrile (0.327 g, 0.8 mmol) was stirred in 1,2,2-trimethylpropylamine (1 ml) for 22 h at 100° C. under nitrogen in a sealed flask. Work up as described in Example 1, 2) gave 182 mg (49%) of the title compound. Mp 160.5–162° C. $^1$H NMR (200 MHz, CDCl$_3$): δ=0.78 (s, 9H), 0.9 (d, 3H), 3.22 (m, 1H), 6.0 (br s, 2H), 6.48 (m, 2H), 6.78 (br d, 1H), 7.48 (d,2H), 7.83 (d, 2H). MA C$_{22}$H$_{24}$ClN$_3$O$_4$S.0.30 H$_2$O (corrected bruttoformula); calc 56.54%; C, 5.31%; H, 8.99%; N; found: 56.47%; C, 5.25%; H, 8.90%; N.

Example 9

3-(3,5-Bis(trifluoromethyl)phenylamino)-2-methylsulfonyl-3-(1,2,2-trimethylpropylamino)-propenenitrile 1) 3-(3,5-Bis(trifluoromethyl)phenylamino)-2-methanesulfonyl-3-methylsulfanyl-2-propenenitrile To a solution of methanesulfonylacetonitrile (0.55 g, 4.6 mmol) in dry acetone (10 ml) first dry potassium carbonate (1.28 g, 9.3 mmol) and then 3,5-bis(trifluoromethyl)phenyl isothiocyanate (1,32 g, 4.7 mmol) were added. The resulting mixture was stirred at room temperature under nitrogen for 4 h, and then filtered. To the filtrate methyl iodide (0.86 ml, 13.9 mmol) was added. The mixture was stirred at room temperature for 2 h. The reaction mixture was filtered and the filtrate was concentrated. The residue was dissolved in dichloromethane and washed with water. The organic layer was dried (sodium sulfate) and concentrated. The residue was recrystallised from ethyl acetate/heptane 1:2 to give the title compound (1.55 g, 83%). Mp 129–131° C. $^1$H NMR (200 MHz, CDCl$_3$): δ=2.35 (s, 3H), 3.25 (s, 3H), 7.77 (s, 2H), 7.80 (s, 1H)H), 9.90 (br s, 1H); EI SP/MS: 404 (M+).

2) 3-(3,5-Bis(trifluoromethyl)phenylamino)-2-methylsulfonyl-3-(1,2,2-trimethylpropylamino)-propenenitrile 3-(3,5-Bis(trifluoromethyl)phenylamino)-2-methylsulfonyl-3-methylsulfanyl-2-propenenitrile (0.225 g, 0.56 mmol) was stirred in 1,2,2-trimethylpropylamine (1 ml) for 22 h at 100° C. under nitrogen in a sealed flask. The reaction mixture was concentrated and the residue dissolved in DCM, washed twice with 1N aqueous HCl and once with water. The organic phase was dried (sodium sulfate) and concentrated. The residue was crystallised from ethyl acetate/heptane 1:4 to give 146 mg (57%) of the title compound. Mp 184.5–188.5° C. $^1$H NMR (200 MHz, CDCl$_3$): δ=0.9 (s, 9H), 1.03 (d, 3H), 3.0 (m, 1H), 7.52 (s, 2H), 7.68 (s, 1H); EI SP/MS: 457 (M+).

Example 10

2-(4-Chlorophenylsulfonyl)-3-(3,5dimethoxyphenylamino)-3-(1,2,2-trimethylpropylamino)-2-propenenitrile

1) 2-(4-Chlorophenylsulfonyl)-3-(3,5-dimethoxyphenylamino)-3-methylsulfanyl-2-propenenitrile To a solution of 4-chlorophenylsulfonylacetonitrile (1.00 g, 4.6 mmol) in dry acetone (10 ml) first dry potassium carbonate (1.28 g, 9.3 mmol) and then 3,5-dimethoxyphenyl isothiocyanate (0.96 g, 4.9 mmol) were added. The resulting mixture was stirred at room temperature under nitrogen for 2 h 15 min and then filtered. To the filtrate methyl iodide (0.86 ml, 13.9 mmol) was added. The mixture was stirred at room temperature for 4 h. The reaction mixture was concentrated. The residue was dissolved in DCM, washed with water, dried (Na$_2$SO$_4$) and concentrated. The residue was crystallised from ethyl acetate/heptane 1:2 to give 1.27 g (65%) of the title compound. Mp 119.5–123° C.; $^1$H NMR (200 MHz, CDCl$_3$): δ=2.29 (s, 3H), 3.80 (s, 6H), 3.36 (m, 3H), 7.53 (d, 2H), 7.87 (d, 2H), 9.82 (br s, 1H); EI SP/MS: 424 (M+).

2) 2-(4-Chlorophenylsulfonyl)-3-(3,5-dimethoxyphenylamino)-3-(1,2,2-trimethylpropylamino)-2-propenenitrile 2-(4-Chlorophenylsulfonyl)-3-(3,5-dimethoxyphenylamino)-3-methylsulfanyl-2-propenenitrile (0.34 g, 0.8 mmol) was stirred in 1,2,2-trimethylpropylamine (1 ml) for 22 h at 75° C. under nitrogen. Work up as described in EXAMPLE 1, 2) gave 264 mg (72%) of the title compound. Mp 177.5–179° C. $^1$H NMR (200 MHz, CDCl$_3$): δ=0.82 (s, 9H), 0.95 (d, 3H), 3.2 (m, 1H), 6.13 (d, 2H), 6.32 (t, 1H), 7.45 (d, 2H), 7.82 (d, 2H); EI SP/MS: 478 (M+).

Example 11

3-[N-(3,5-bis(trifluoromethyl)phenyl)-N-methylamino]-2-(4-chlorophenylsulfonyl)-3-(1,2,2-trimethylpropylamino)-2-propenenitrile

1) 3-[N-(3,5-Bis(trifluoromethyl)phenyl)-N-methylamino]-2-(4-chlorophenylsulfonyl)-3-methylsulfanyl-2-propenenitrile To a solution of 4-chlorophenylsulfonylacetonitrile (1.10 g, 5.1 mmol) in dry acetone (12 ml) first dry potassium carbonate (1.41 g, 10.2 mmol) and then 3,5-bis(trifluoromethyl)phenyl isothiocyanate (1,44 g, 5.3 mmol) were added. The resulting mixture was stirred at room temperature under nitrogen. After 2 h methyl iodide (3.80 ml, 61.2 mmol) was added. The mixture was stirred at room temperature for 18 h, followed by filtration and concentration. Crystallisation from ethyl acetate/heptane 1:3 gave 0.52 g (20%) of the title compound. $^1$H NMR (300 MHz, CDCl$_3$): δ=2.40 (s, 3H), 3.65 (s, 3H), 7.36 (s, 2H), 7.42 (d, 2H), 7.58 (s, 1H), 7.65 (d, 2H);); EI SP/MS: 514 (M+).

2) 3-[N-(3,5-Bis(trifluoromethyl)phenyl)-N-methylamino]-2-(4-chlorophenylsulfonyl)-3-(1,2,2-trimethylpropylamino)-2-propenenitrile To a solution of 3-[N-(3,5-Bis(trifluoromethyl)phenyl)-N-methylamino]-2-(4-chloro-phenylsulfonyl)-3-methylsulfanyl-2-propenenitrile (0.300 g, 0.58 mmol) in dry acetonitrile (2 ml) was added 1,2,2-trimethylpropylamine (0.12 g) and dry triethylamine (89 μl). The mixture was stirred for 68 h at 80° C. under nitrogen. The reaction mixture was concentrated. Purification by flash chromatography using ethyl acetate/heptane 1:4 and 1:3 as eluent gave a syrup (142 mg) which was crystallised in ethanol/water to give 110 mg (33%) of the title compound. Mp 151.5–154° C. $^1$H NMR (300 MHz, CDCl$_3$): δ=0.9 (s, 9H), 1.10 (d, 3H), 3.11 (m, 1H), 3.30 (s, 3H), 7.10 (s, 2H), 7.46 (s, 1H), 7.55 (d, 2H), 7.85 (d, 2H), 8.1 (br d, 1H); MA calc for C$_{24}$H$_{24}$ClF$_6$N$_3$O$_2$S: C, 50.75%; H, 4.26%; N, 7.40%; Cl, 6.24%. Found: C, 50.79%; H, 4.28%; N, 7.24%; Cl, 6.19%.

Example 12

(1'S,2'S)-3-[2-Benzyloxycyclopentylamino]-3-[3,5-bis(trifluoromethyl)phenylamino]-2-(4-chlorophenylsulfonyl)-2-propenenitrile 3-(3,5-Bis(trifluoromethyl)phenylamino)-2-(4-chlorophenylsulfonyl)-3-methylsulfanyl-2-propenenitrile (0.150 g, 0.3 mmol) was stirred in (1S,2S)-2-benzyloxycyclopentylamine (0.3 ml) at 80° C. in a sealed flask for 20 h. Work up as described in Example 1, 2) gave 108 mg (53%) of the title compound as white crystals. $^1$H NMR (300 MHz, CDCl$_3$): d=1.6–1.75 (m, 4H), 2.05 (m, 2H), 3.9 (m,1H), 4.1 (m, 1H), 4.5 (dd, 2H), 7.15 (s, 1H), 7.2 (m, 6H), 7.5 (d, 2H), 7.7 (m, 3H), 8.2 (s, 1H), 9.8 (s, 1H).

Example 13

(1'R,2'R)-3-[2-Benzyloxycyclopentylamino]-3-[3,5-bis(trifluoromethyl)phenylamino]-2-(4-chlorophenylsulfonyl)-2-propenenitrile 3-(3,5-Bis(trifluoromethyl)phenylamino)-2-(4-chlorophenylsulfonyl)-3-methylsulfanyl-2-propenenitrile (0.150 g, 0.3 mmol) was stirred in (1R,2R)-2-benzyloxycyclopentylamine (0.3 ml) at 80° C. in a sealed flask for 20 h. Work up as described in Example 1, 2) gave 106 mg (51%) of the title compound as white crystals. $^1$H NMR (300 MHz, CDCl$_3$): d=1.6–1.75 (m, 4H), 2.0 (m, 2H), 3.85 (m,1H), 4.15 (m, 1H), 4.5 (dd, 2H), 6.9 (s, 1H), 7.15–7.30 (m, 6H), 7.35 (d, 1H), 7.5 (d, 2H), 7.7 (d, 1H),8.5 (br s, 1H).

Example 14

(S)-3-[3,5-Bis(trifluoromethyl)phenylamino]-2-(4-chlorophenylsulfonyl)-3-(1,2,2-trimethylpropylamino)-2-propenenitrile 3-(3,5-Bis(trifluoromethyl)phenylamino)-2-(4-chlorophenylsulfonyl)-3-methylsulfanyl-2-propenenitrile (0.200 g, 0.4 mmol) was stirred in (S)-1,2,2-trimethylpropylamine (0.2 ml) at 80° C. in a sealed flask for 20 h. Work up as described in Example 1, 2) gave 25 mg (11%) of the title compound as white crystals. $^1$H NMR (300 MHz, CDCl$_3$): d=0.95 (s, 9H), 1.15 (d, 3H), 3.0 (m, 1H), 7.40 (s, 2H), 7.50 (d, 2H), 7.70 (s,1H), 7.82 (d, 2H).

Example 15

(S)-3-[3,5-Bis(trifluoromethyl)phenylamino]-2-(4-chlorophenylsulfonyl)-3-(1,2-dimethylpropylamino)-2-propenenitrile 3-(3,5-Bis(trifluoromethyl)phenylamino)-2-(4-chlorophenylsulfonyl)-3-methylsulfanyl-2-propenenitrile (0.200 g, 0.4 mmol) was stirred in (S)-1,2-dimethylpropylamine (0.2 ml) at 80° C. in a sealed flask for 20 h. Work up as described in Example 1, 2) gave 40 mg (18%) of the title compound as white crystals. $^1$H NMR (300 MHz, CDCl$_3$): d=0.85 (dd, 6H), 1.05 (d, 3H), 1.7 (m,1H) 3.10 (m, 1H), 7.43 (s, 2H), 7.48 (d, 2H), 7.70 (s, 1H), 7.80 (d, 2H).

Example 16

(R)-3-[3,5-Bis(trifluoromethyl)phenylamino]-2-(4-chlorophenylsulfonyl)-3-(1,2-dimethylpropylamino)-2-propenenitrile 3-(3,5-Bis(trifluoromethyl)phenylamino)-2-(4-chlorophenylsulfonyl)-3-methylsulfanyl-2-propenenitrile (0.200 g, 0.4 mmol) was stirred in (R)-1,2-dimethylpropylamine (0.2 ml) at 80 ° C. in a sealed flask for 20 h. Work up as described in Example 1,2) gave 30 mg (13%) of the title compound as white crystals.

$^1$H NMR (300 MHz, CDCl$_3$): d=0.9 (dd, 6H), 1.05 (d, 3H), 1.7 (m, 1H),3.15 (m,1H) 7.45 (s, 2H), 7.50 (d, 2H), 7.65 (s, 1H), 7.79 (d, 2H).

Example 17

Synthesis of 3-[3,5-Bis(trifluoromethyl)phenylamino]-2-(4-chlorophenylsulfonyl)-3-(1,1-dimethylpropylamino)-2-propenenitrile 3-(3,5-Bis(trifluoromethyl)phenylamino)-2-(4-chlorophenylsulfonyl)-3-methylsulfanyl-2-propenenitrile (0.300 g, 0.6 mmol) was stirred in 1,1-dimethylpropylamine (1 ml) for 40 h at 60° C. and for 43 h at 110° C. under nitrogen. The reaction mixture was concentrated and the residue dissolved in DCM, washed twice with 1N aqueous HCl and once with water. The organic phase was dried (sodium sulfate) and concentrated. The residue was purified by flash chromatography using from ethyl acetate/heptane 1:2 as eluent followed recrystallisation from ethyl acetate/heptane 1:2 to give 25 mg (8%) of the title compound. Mp 205–207° C. $^1$H NMR (200 MHz, CDCl$_3$): δ=0.98 (t, 3H), 1.54 (s, 6H), 1.68 (q, 2H), 7.10 (s, 2H), 7.53 (d, 2H), 7.60 (s, 1H), 7.81 (d, 2H); EI SP/MS: 539 (M+).

Example 18

Synthesis of 3-[3,5-Bis(trifluoromethyl)phenylamino]-2-(4-chlorophenylsulfonyl)-3-(5-cyclopropyl-2-methyl-2H-pyrazol-3-ylamino)-2-propenenitrile To a solution of 3-(3,5-bis(trifluoromethyl)phenylamino)-2-(4-chloro-phenylsulfonyl)-3-methylsulfanyl-2-propenenitrile (0.300 9, 0.6 mmol) in dry acetonitrile (1.0 ml), triethylamine (0.100 ml, 0.7 mmol) and 5-amino-3-cyclopropyl-1-methyl pyrazole (0.100 g, 0.7 mmol) were added. The reaction mixture was stirred for 41 h at 80° C. under nitrogen and then concentrated. The residue was worked up as described in Example 17,2) to give 90 mg (25%) of the title compound. $^1$H NMR (200 MHz, CDCl$_3$): δ=0.7 (m, 2H), 0.9 (m, 2H), 1.85 (m, 1H), 3.5 (s, 3H), 5.3 (s, 1H), 5.4 (s, 1H), 5.85 (s, 1H), 7.28 (s, 2H), 7.53 (d, 2H), 7.63 (s, 1H), 7.8 (d, 2H); EI SP/MS: 589 (M+).

Example 19

Synthesis of (R)-3-[3,5-bis(trifluoromethyl)phenylamino]-2-(4-chlorophenylsulfonyl)-3-(1,2,2-trimethylpropylamino)-2-propenenitrile 3-(3,5-Bis(trifluoromethyl)phenylamino)-2-(4-chlorophenylsulfonyl)-3-methylsulfanyl-2-propenenitrile (0.300 g, 0.6 mmol) was stirred in (R)-1,2,2-trimethylpropylamine (1 ml) for 17 h at 75° C. under nitrogen. Work-up as described in Example 17, 2) gave 131 mg (39%) of the title compound. Mp 164–165° C. $^1$H NMR (200 MHz, CDCl$_3$): δ=0.9 (s, 9H), 1.0 (d, 3H), 3.0 (m, 1H), 7.37 (s, 2H), 7.50 (d, 2H), 7.68 (s, 1H), 7.80 (d, 2H); Analysis: calc. for $C_{23}H_{22}ClF_6N_3O_2S$: C, 49.87%; H, 4.00%; N, 7.59%. Found: C, 49.95%; H, 4.15%; N, 7.48%.

Example 20

Synthesis of 3-(3,5-Bis(trifluoromethyl)phenylamino)-3-isopropylamino-2-methylsulfonyl-propenenitrile 3-(3,5-Bis(trifluoromethyl)phenylamino)-2-methanesulfonyl-3-methylsulfanyl-2-propenenitrile (0.323 g, 0.8 mmol) was stirred in isopropylamine (1 ml) for 17 h at 75° C. under nitrogen. Work-up as described in Example 17, 2) without chromatography gave 247 mg (74%) of the title compound. Mp 188.5–191° C. $^1$H NMR (200 MHz, CDCl$_3$): δ=1.15 (d, 6H), 3.15 (s, 3H), 3.40 (m, 1H), 7.56 (s, 2H), 7.68 (s, 1H). Analysis: calc. for $C_{15}H_{15}F_6N_3O_2S$: C, 43.38%; H, 3.64%; N, 10.12%. Found: C, 43.52%; H, 3.63%; N, 9.98%.

Example 21

Synthesis of (R)-3-[3,5-bis(trifluoromethyl)phenylamino]-2-methanesulfonyl-3-(1,2,2-trimethylpropylamino)-2-propenenitrile 3-(3,5Bis(trifluoromethyl)phenylamino)-2-methanesulfonyl)-3-methylsulfanyl-2-propenenitrile (0.250 g, 0.6 mmol) was stirred in (R)-1,2,2-trimethylpropylamine (1 ml) for 17 h at 75° C. and 17 h at 100° C. under nitrogen. Work-up as described in Example 17, 2) without chromatography gave 104 mg (38%) of the title compound. Mp 181–181.5° C. $^1$H NMR (200 MHz, CDCl$_3$): δ=0.9 (s, 9H), 1.03 (d, 3H), 3.0 (m, 1H), 3.15 (s, 3H), 7.52 (s, 2H), 7.71 (s, 1H); Analysis: calc. for $C_{18}H_{21}F_6N_3O_2S$: C, 47.26%; H, 4.63%; N, 9.19%. Found: C, 47.43%; H, 4.75%; N, 9.12%.

Example 22

Synthesis of (S)-3-[3,5-bis(trifluoromethyl) phenylamino]-2-methanesulfonyl-3-(1,2,2-trimethylpropylamino)-2-propenenitrile 3-(3,5-Bis(trifluoromethyl)phenylamino)-2-methanesulfonyl)-3-methylsulfanyl-2-propenenitrile (0.250 g, 0.6 mmol) was stirred in (S)-1,2,2-trimethylpropylamine (1 ml) for 19 h at 75° C. and 4 days at room temperature under nitrogen. Work-up as described in Example 17, 2) without chromatography gave 71 mg (26%) of the title compound. Mp 180.5–181.5° C. $^1$H NMR (200 MHz, CDCl$_3$): δ=0.9 (s, 9H), 1.03 (d, 3H), 3.0 (m, 1H), 3.15 (s, 3H), 7.52 (s, 2H), 7.71 (s, 1H); Analysis: calc. for $C_{18}H_{21}F_6N_3O_2S$: C, 47.26%; H, 4.63%; N, 9.19%. Found: C, 47.48%; H, 4.76%; N, 9.18%.

Example 23

Synthesis of 2-(4-Chlorophenylsulfonyl)-3-(3,5-dimethoxyphenylamino)-3-(1,1-dimethylpropylamino)-2-propenenitrile 2-(4-Chlorophenylsulfonyl)-3-(3,5-dimethoxyphenylamino)-3-methylsulfanyl-2-propenenitrile (0.30 g, 0.7 mmol) was stirred in 1,1-dimethylpropylamine (1 ml) for 17 h at 100° C. in a sealed flask under nitrogen. Work-up as described in Example 17, 2) without chromatography gave 84 mg (26%) of the title compound. Mp 189–190° C. $^1$H NMR (200 MHz, CDCl$_3$): δ=0.95 (t, 3H), 1.35 (s, 6H), 1.65 (q, 2H), 3.62 (s, 6H), 6.20 (t, 1H) 6.45 (br s, 1H), 7.0 (br s, 1H), 7.50 (dt, 2H), 7.83 (dt, 2H); Analysis: calc. for $C_{22}H_{26}ClN_3O_4S$: C, 59.96%; H, 5.65%; N, 9.06%. Found: C, 56.82%; H, 5.64%; N, 8.90%.

Example 24

Synthesis of 2-(4-Chlorophenylsulfonyl)-3-(3,5-dimethoxyphenylamino)-3-cyclobutylamino-2-propenenitrile 4-(Chlorophenylsulfonyl)-3-(3,5-dimethoxyphenylamino)-3-methylsulfanyl-2-propenenitrile (0.99 g, 2.4 mmol), cyclobutylamine (0.60 ml, 7.2 mmol) and acetonitrile (4 ml) was stirred for 17 h at 100° C. in a sealed flask under nitrogen. Work-up as described in Example 17, 2) without chromatography gave 0.90 g (83%) of the title compound. Mp 163.5–164.5° C. $^1$H NMR (200 MHz, CDCl$_3$): δ=1.6 (m, 2H), 1.85 (m, 2H), 2.1 (m, 2H), 3.77 (s, 6H), 3.8 (m, 1H), 6.12 (d, 2H), 6.32 (t, 1H), 7.47 (dt, 2H), 7.81 (dt, 2H); Analysis: calc. for $C_{21}H_{22}ClN_3O_4S$: C, 56.31%; H, 4.95%; N, 9.38%. Found: C, 56.40%; H, 4.99%; N, 9.30%.

Example 25

Synthesis of 3-(3,5-dimethoxyphenylamino)-2-methanesulfonyl-3-(1,2,2-trimethylpropylamino)-propenenitrile 1) 3-(3,5-Dimethoxyphenylamino)-2-methanesulfonyl-3-methylsulfanyl-2-propenenitrile To a solution of methanesulfonylacetonitrile (0.55 g, 4.6 mmol) in dry acetone (10 ml) first dry potassium carbonate (1.28 g, 9.3 mmol) and then 3,5-dimethoxyphenyl isothiocyanate (0.96 g, 4.9 mmol) were added. The resulting mixture was stirred at room temperature under nitrogen for 23 h, then filtered and washed with ethanol. To the filtrate methyl iodide (0.86 ml, 13.9 mmol) was added. The mixture was stirred at room temperature for 4 h. The reaction mixture was filtered and the filtrate was concentrated. The residue was dissolved in dichloromethane and washed with water. The organic layer was dried (sodium sulfate) and concentrated. The residue was recrystallised from ethyl acetate to give the title compound (0.728 g, 48%). $^1$H NMR (200 MHz, CDCl$_3$): δ=2.27 (s, 3H), 3.19 (s, 3H), 3.80 (s, 6H), 6.48 (t, 1H), 6.44 (d, 2H) EI SP/MS: 328 (M+).

2) 3-(3,5-Dimethoxyphenylamino)-2-methanesulfonyl-3-(1,2,2-trimethylpropylamino)-propenenitrile 3-(3,5-dimethoxyphenylamino)-2-methanesulfonyl-3-methylsulfany-2-propenenitrile (0.263 g, 0.8 mmol) was stirred in 1,2,2-trimethylpropylamine (1 ml) for 17 h at 75° C. under nitrogen. Work-up as described in Example 17, 2) gave the title compound as a syrup, 262 mg (86%). $^1$H NMR (200 MHz, CDCl$_3$): δ=0.85 (s, 9H), 1.01 (d, 3H), 3.12 (s, 3H), 3.26 (m, 1H), 3.78 (s, 6H), 6.25 (d, 2H), 6.35 (t, 1H); EI SP/MS: 381 (M+).

Example 26

Synthesis of 3-(3,5-dimethoxyphenylamino)-3-isopropyl-2-methanesulfonyl-propenenitrile 3-(3,5-dimethoxyphenylamino)-2-methanesulfonyl-3-methylsulfanyl-2-propenenitrile (0.263 g, 0.8 mmol) was stirred in isopropylamine (1 ml) for 17 h at 75° C. under nitrogen. Work-up as described in Example 17, 2) to give the title compound syrup, 209 mg (77%). Mp 135–136.5° C. $^1$H NMR (200 MHz, CDCl$_3$): δ=1.15 (s, 6H), 3.10 (s, 3H), 3.5 (m, 1H), 3.78 (s, 6H), 6.25 (br s, 2H), 6.33 (br s, 1H); Analysis: calc. for $C_{15}H_{21}N_3O_4S$: C, 53.08%; H, 6.24%; N, 12.38%. Found: C, 53.38%; H, 6.26%; N, 12.31%.

Example 27

Synthesis of 3-(Benzo[1,3]dioxol-5-ylamino)-3-(1,1-dimethyl-propylamino)-2-(4-chloro-phenylsulfonyl)-propenenitrile 1) 3-(Benzo[1,3]dioxol-5-ylamino)-2-(4-chlorophenylsulfonyl)-3-methylsulfanyl-2-propenenitrile To a solution of 4-chlorophenylsulfonylacetonitrile (1.00 g, 4.64 mmol) in dry acetone (10 ml) first dry potassium carbonate (1.28 g, 9.3 mmol) and then 3,4-methylenedioxyphenyl isothiocyanate (0.87 g, 4.9 mmol) were added. The resulting mixture was stirred at room temperature under nitrogen for 4 h, and then filtered. To the filtrate methyl iodide (0.86 ml, 13.9 mmol) was added. The mixture was stirred at room temperature for 50 min. Then pH was adjusted to 1 with 1N aqueous HCl. The precipitate was filtered off and washed with water to give 1.12 g (59%) of the title compound. Mp 196–200° C. (decomp.); $^1$H NMR (200 MHz, CDCl$_3$): δ=2.22 (s, 3H), 6.05 (s, 2H), 6.68 (m, 2H), 6.80 (d, 1H), 7.53 (d, 2H), 7.87 (d, 2H), 9.80 (br s, 1H); EI SP/MS: 408 (M+).

2) 3-(Benzo[1,3]dioxol-5-ylamino)-3-(1,1-dimethyl-propylamino)-2-(4-chlorophenylsulfonyl)-propenenitrile 3-(Benzo[1,3]dioxol-5-ylamino-2-(4-chloro-phenylsulfonyl)-3-methylsulfanyl-2-propenenitrile (0.327 g, 0.8 mmol) was stirred in 1,2,2-trimethylpropylamine (1 ml) for 17 h at 100° C. under nitrogen in a sealed flask. Work-up as described in EXAMPLE 17, 2) without chromatography gave 81 mg (26%) of the title compound. Mp 169–170° C. $^1$H NMR (200 MHz, CDCl$_3$): δ=0.95 (t, 3H), 1.37 (s, 6H), 1.65 (q, 2H), 5.98 (s, 1H), 6.2 (m, 2H), 6.45 (br s, 1H), 6.66 (d, 1H), 6.98 (br s, 1H), 7.50 (d, 2H), 7.80 (d, 2H). Analysis: calc. for C$_{21}$H$_{22}$ClN$_3$O$_4$S 0.50H$_2$O (corrected formula): C, 55.20%; H, 5.07%; N, 9.20%; Found: C, 55.18%; H, 4.90%; N, 8.90%.

Example 28

Synthesis of 3-(Benzo[1,3]dioxol-5-ylamino)-3-cyclobutylamino-2-(4-chloro-phenylsulfonyl)-propenenitrile 3-(Benzo[1,3]dioxol-5-ylamino-2-(4-chloro-phenylsulfonyl)-3-methylsulfanyl-2-propenenitrile (0.29 g, 0.7 mmol) was stirred in cyclobutylamine (0.6 ml 7.0 mmol) for 17 h at 100° C. under nitrogen in a sealed flask. The reaction mixture was concentrated and the residue was crystallised from ethyl acetate to give 88 mg (29%) of the title compound. Mp 189.5° C. $^1$H NMR (200 MHz, CDCl$_3$): δ=1.6 (m, 2H), 1.75 (m, 2H), 2.05 (m, 2H), 3.80 (m, 1H), 6.02 (s, 2H), 6.5 (m, 2H), 6.79 (d, 2H), 7.50 (dt, 2H), 7.83 (dt, 2H). Analysis: calc. for C$_{20}$H$_{18}$ClN$_3$O$_4$S: C, 55.62%; H, 4.20%; N, 9.73%; Found: C, 55.59%; H, 4.21%; N, 9.59%.

Example 29

Synthesis of 2-(4-Chlorophenylsulfonyl)-3-(3,5-dichlorophenylamino)-3-(1,1-dimethylpropylamino)-2-propenenitrile 2-(4-Chloro-phenylsulfonyl)-3-(3,5-dichlorophenylamino)-3-methylsulfanyl-2-propenenitrile (0.359 g, 0.8 mmol) was stirred in 1,2,2-trimethylpropylamine (0.125 ml) for 22 h at 50° C. and for 18 h at 80° C. under nitrogen in a sealed flask. Work-up as described in EXAMPLE 17, 2) gave 64 mg (17%) of the title compound. Mp 189–191.5° C. (EtOAc). $^1$H NMR (200 MHz, CDCl$_3$): δ=0.99 (t, 3H), 1.38 (s, 6H), 1.68 (q, 2H), 6.26 (br s, 1H), 6.50 (d, 2H), 7.10 (t, 1H), 7.55 (dt, 2H), 7.81 (dt, 2H); EI SP/MS: 475 (M+4), 473 (M+2), 471 (M+).

Example 30

Synthesis of 2-(4-Chlorophenylsulfonyl)-3-cyclobutylamino-3-(3,5-dichlorophenylamino)-2-propenenitrile 2-(4-Chloro-phenylsulfonyl)-3-(3,5-dichlorophenylamino)-3-methylsulfanyl-2-propenenitrile (0.90 g, 2.1 mmol), cyclobutylamine (0.50 ml, 6.3 mmol) and acetonitrile (2 ml) were stirred for 40 h at 100° C. under nitrogen in a sealed flask. Work-up as described in EXAMPLE 17, 2) gave 0.47 g (49%) of the title compound. 179.5–181.5° C. (EtOAc) $^1$H NMR (200 MHz, CDCl$_3$): δ=1.65 (m, 2H), 1.95 (m, 2H), 2.1 (m, 2H), 3.65 (sextet, 1H), 6.88 (d, 2H), 7.18 (t, 1H), 7.47 (d, 2H), 7.78 (d, 2H); EI SP/MS: 459 (M+4), 357 (M+2) 455 (M+).

Example 31

Synthesis of 3-sec-Butylamino-2-(4-chlorophenylsulfonyl)-3-(3,5-dichlorophenylamino)-2-propenenitrile 2-(4-Chloro-phenylsulfonyl)-3-(3,5-dichlorophenylamino)-3-methylsulfanyl-2-propenenitrile (0.50 g, 1.2 mmol) was stirred in 2-aminobutane (1 ml) for 17 h at 100° C. under nitrogen in a sealed flask. Work-up as described in EXAMPLE 17, 2) without chromatography gave 0.38 g (69%) of the title compound. Mp 150–152 ° C. $^1$H NMR (200 MHz, CDCl$_3$): δ=0.85 (t, 3H), 1.06 (d, 3H), 1.48 (p, 2H), 3.25 (m, 1H), 6.90 (d, 2H), 7.20 (t, 1H), 7.47 (d, 2H), 7.78 (d, 2H); EI SP/MS: 457 (M+), 459 (M+2), 461 (M+4).

Example 32

Synthesis of 3-(3-Methoxy-5-trifluoromethyl-phenylamino)-2-methylsulfonyl-3-(1,2,2-trimethylpropylamino)-propenenitrile 1) 3-(3-Methoxy-5-trifluoromethyl-phenylamino)-2-methylsulfonyl-3-methylsulfanyl-propenenitrile To a solution of 3-methoxy-5-trifluoromethyl-anilin(1.50 g, 7.8 mmol) in dry ethyl acetate (10 ml) thiophosgene (0.20 ml, 2.6 mmol) was added dropwise. After stirring for 1.5 h at 75° C. the reaction mixture was cooled on an ice bath and then filtered. The filtrate was concentrated. The residue was dissolved in dry acetone (5 ml) and added to a suspension of methanesulfonylacetonitrile (0.34 g, 2.6 mmol) and dry potassium carbonate (0.72 g, 5.2 mmol) in dry acetone (5 ml). The resulting mixture was stirred at room temperature under nitrogen for 19 h, and then filtered. To the filtrate methyl iodide (0.49 ml, 7.8 mmol) was added. The mixture was stirred at room temperature for 1.5 h. The reaction mixture was concentrated and the residue was taken up into dichloromethane and water. The organic layer was washed with water (2x), dried (sodium sulfate) and concentrated. The residue was recrystallised from ethyl acetate to give 0.70 g (73%) of the title compound. $^1$H NMR (200 MHz, CDCl$_3$): δ=2.28 (s, 3H), 3.22 (s, 3H), 3,87 (s, 3H), 7.0 (t, 1H), 7.05 (br s, 1H), 7.14 (br s, 1H), 9.8 (br s, 1H); EI SP/MS: 366 (M−2).

2) 3-(3-Methoxy-5-trifluoromethyl-phenylamino)-2-methylsulfonyl-3-(1,2,2-trimethylpropylamino)-acrylonitrile 3-(3-Methoxy-5-trifluoromethyl-phenylamino)-2-methylsulfonyl-3-methylsulfanyl-propenenitrile (0.22 g, 0.6 mmol) was stirred in 1,2,2-trimethylpropylamine (1 ml) for 17 h at 75° C. under nitrogen. Work-up as described in EXAMPLE 17, 2) without chromatography gave 100 mg (40%) of the title compound. Mp 110–113° C. $^1$H NMR (200 MHz, CDCl$_3$): δ=0.87 (s, 9H), 1.01 (d, 3H), 3.08 (m, 1H), 3.10 (s, 3H), 3.87 (s, 3H), 6.81 (br s, 1H), 6.95 (br s, 1H), 6.97 (br s, 1H); Analysis: calc. for C$_{18}$H$_{24}$N$_3$O$_3$S: C, 51.54%; H, 5.77%; N, 10.02%; Found: C, 51.77%; H, 6.05%; N, 9.80%.

Example 33

Synthesis of 3-(3-Fluoro-5-trifluoromethyl-phenylamino)-2-methylsulfonyl-3-(1,2,2-trimethylpropylamino)-propenenitrile 1) 3-(3-Fluoro-5-trifluoromethylphenylamino)-2-methylsulfonyl-3-methylsulfanyl-propenenitrile To a solution of 3-fluoro-5-trifluoromethyl-anilin(1.50 g, 8.3 mmol) in dry ethyl acetate (5 ml) thiophosgene (0.215 ml, 2.8 mmol) was added dropwise. After stirring for 1.5 h at 75° C., the reaction mixture was cooled on an ice bath and then filtered. The filtrate was concentrated. The residue was dissolved in dry acetone (5 ml) and added to a suspension of methanesulfonylacetonitrile (0.33 g, 2.8 mmol) and dry potassium carbonate (0.77 g, 5.6 mmol) in dry acetone (5 ml). The resulting mixture was stirred at room temperature under nitrogen for 22 h, and then filtered. To the filtrate methyl iodide (0.525 ml, 8.4 mmol) was added. The mixture was stirred at room temperature for 2 h. The reaction mixture was filtered, the filtrate was concentrated and the residue was taken up into dichloromethane and water. The organic layer was washed with water (2×), dried (sodium sulfate) and concentrated. The residue was recrystallised from ethyl acetate to give 0.297 g (30%) of the title compound. $^1$H NMR (200 MHz, CDCl$_3$): δ=2.32 (s, 3H), 3.21 (s, 3H), 7.28 (s, 1H), 7.32 (br s, 1H), 7.37 (br s, 1H), 9.85 (br s, 1H); EI SP/MS: 354 (M+).

2) 3-(3-Fluoro-5-trifluoromethyl-phenylamino)-2-methylsulfonyl-3-(1,2,2-trimethylpropylamino)-propenenitrile 3-(3-Fluoro-5-trifluoromethylphenylamino)-2-methylsulfonyl-3-methylsulfanyl-propenenitrile (0.176 g, 0.5 mmol) was stirred in 1,2,2-trimethylpropylamine (1 ml) for 17 h at 75° C. under nitrogen. Work-up as described in EXAMPLE 17, 2) without chromatography gave 98 mg (49%) of the title compound. Mp 183–1850° C. $^1$H NMR (200 MHz, CDCl$_3$): δ=0.87 (s, 9H), 1.03 (d, 3H), 3.05 (m, 1H), 3.13 (s, 3H) 7.02 (br d, 1H), 7.15 (m, 2H); EI SP/MS: 407 (M+).

Example 34

Synthesis of 3-(4-Chlorophenylamino)-2-methylsulfonyl-3-(1,2,2-trimethylpropylamino)-acrylonitrile 1) 3-(4-Chlorophenylamino)-2-methylsulfonyl-3-methylsulfanyl-propenenitrile To a solution of methanesulfonylacetonitrile (0.55 g, 4.9 mmol) in dry acetone (5 ml) first dry potassium carbonate (1.28 g, 9.3 mmol) and then 4-chlorophenyl isothiocyanate (0.78 g, 4.6 mmol) were added. The resulting mixture was stirred at room temperature under nitrogen for 22 h, and then filtered. To the filtrate methyl iodide (0.86 ml, 13.9 mmol) was added. The mixture was stirred at room temperature for 2 h. The precipitate was filtered off, the filtrate was concentrated. The residue was taken up into dichloromethane and water. The organic layer was washed with water (2×), dried (sodium sulfate) and concentrated. Crystallisation from ethyl acetate gave 1.114 g (80%) of the title compound. $^1$H NMR (200 MHz, CDCl$_3$): δ=2.25 (s, 3H), 3.20 /s, 3H), 7.25 (d, 2H), 7.41 (d, 2H), 9.70 (br s, 1H); EI SP/MS: 302 (M+), 304 (M+2).

2) 3-(4-Chlorophenylamino)-2-methylsulfonyl-3-(1,2,2-trimethylpropylamino)-propenenitrile 3-(4-Chlorophenylamino)-2-methylsulfonyl-3-methylsulfanyl-propenenitrile (0.242 g, 0.8 mmol) was stirred in 1,2,2-trimethylpropylamine (1 ml) for 17 h at 75° C. under nitrogen. Work-up as described in EXAMPLE 17, 2) without chromatography gave 0.240 g (85%) of the title compound. Mp 160.5–161.5° C. $^1$H NMR (200 MHz, CDCl$_3$): δ=0.87 (s, 9H), 0.97 (d, 3H), 3.1 (m, 4H), 7.07 (d, 1H), 7.49 (d, 2H); Analysis: calc. for C$_{16}$H$_{22}$ClN$_3$O$_2$S: C, 54.00%; H, 6.23%; N, 11.81%; Found: C, 54.26%; H, 6.33%; N, 11.76%.

Example 35

Synthesis of 3-(Benzothiazol-6-ylamino)-3-(1,1-dimethyl-propylamino)-2-methylsulfonyl-propenenitrile 1) 3-(benzothiazol-6-ylamino)-2-methylsulfonyl-3-methylsulfanyl-propenenitrile To a solution of 6-aminobenzothiazole (1.00 g, 6.7 mmol) in dry ethyl acetate (10 ml) thiophosgene (0.170 ml, 2.2 mmol) was added dropwise. After stirring for 1.5 h at 75° C., the reaction mixture was cooled on an ice bath and then filtered. The filtrate was concentrated. The residue was dissolved in dry acetone (5 ml) and added to a suspension of methanesulfonylacetonitrile (0.264 g, 2.2 mmol) and dry potassium carbonate (0.61 g, 4.4 mmol) in dry acetone (10 ml). The resulting mixture was stirred at room temperature under nitrogen for 70 h, and then filtered. To the filtrate methyl iodide (0.415 ml, 6.7 mmol) was added. The mixture was stirred at room temperature for 4.5 h. The reaction mixture was filtered, the filtrate was concentrated and the residue was taken up into dichloromethane and water. The organic layer was washed with water (2×), dried (sodium sulfate) and concentrated. The residue was recrystallised from ethyl acetate to give 0.219 g (11%) of the title compound. $^1$H NMR (200 MHz, CDCl$_3$): δ=2.25 (s, 3H), 3.20 (s, 3H), 7.45 (dd, 1H), 7.93 (d, 1H), 8.16 (d, 1H), 9.05 (s, 1H), 9.95 (br s, 1H); EI SP/MS: 325 (M+).

2) 3-(Benzothiazol-6-ylamino)-3-(1,1-dimethyl-propylamino)-2-methylsulfonyl-propenenitrile 3-(Benzothiazol-6-ylamino)-2-methylsulfonyl-3-methylsulfanyl-propenenitrile (0.167 g, 0.5 mmol) was stirred in 1,1-dimethylpropylamine (0.5 ml) for 17 h at 100° C. under nitrogen in a sealed flask. Work-up as described in EXAMPLE 17, 2) without chromatography gave 60 mg (33%) of the title compound. Mp 112–114° C. $^1$H NMR (200 MHz, CDCl$_3$): δ=1.00 (t, 3H), 1.39 (s, 6H), 1.65 (q, 2H), 3.12 (s, 3H) 7.29 (dd, 1H), 7.70 (d, 1H), 8.13 (d, 1H), 9.0 (s, 1H); EI SP/MS: 364 (M+).

Example 36

Synthesis of 3-(Benzo[1,3]dioxol-5-ylamino)-2-(2,2dimethyl-propionyl)-3-(1,1-dimethyl-propylamino)-propenenitrile 1) 3-(Benzo[1,3]dioxol-5-ylamino)-2-(2,2-dimethyl-propionyl)-3-methylsulfanyl-propenenitrile To a solution of 4,4-dimethyl-3-oxopentanenitrile (0.626 g, 5.0 mmol) in dry acetone (10 ml) first potassium carbonate (1.38 g, 10 mmol) and then 3,4-methylendioxyphenyl isothiocyanate (0.941 g, 5.3 mmol) were added. The resulting mixture was stirred at room temperature under nitrogen for 72 h, and then filtered. To the filtrate methyl iodide (0.93 ml, 15 mmol) was added. The mixture was stirred at room temperature for 45 min. The precipitate was filtered off and the filtrate was concentrated. The residue was taken up into dichloromethane and water. The organic layer was washed with water (2×), dried (sodium sulfate) and concentrated. Crystallisation from ethyl acetate/heptane 1:1 gave 1.56 g (98%) of the title compound. Mp 139–141° C.; $^1$H NMR (200 MHz, CDCl$_3$): δ=1.40 (s, 9H), 2.28 (s, 3H), 6.03 (s, 2H), 6.75 (dd, 1H), 6.8 (m, 2H), 13.5 (br s, 1H); EI SP/MS: 318 (M+).

2) 3-(Benzo[1,3]dioxol-5-ylamino)-2-(2,2-dimethyl-propionyl)-3-(1,1-dimethyl-propylamino)-propenenitrile 3-(Benzo[1,3]dioxol-5-ylamino)-2-(2,2-dimethyl-propionyl)-3-methylsulfanyl-propenenitrile (0.500 g, 1.6 mmol) 1,1-dimethylpropylamine (0.275 ml, 2.4 mmol), triethylamine (0.335 ml, 2.4 mmol) in acetonitrile (1 ml) were stirred for 65 h at 100° C. under nitrogen in a sealed flask. Work-up as described in EXAMPLE 17, 2) without chromatography gave 0.130 g (23%) of the title compound. Mp 161–165° C. ¹H NMR (200 MHz, CDCl$_3$): δ=0.96 (t, 3H), 1.30 (s, 9H), 1.35 (s, 6H), 1.65 (q, 2H), 5.98 (s, 2H), 6.57 (dd, 1H), 6.65 (d, 1H), 6.77 (d, 1H), 9.9 (br s, 1H); EI SP/MS: 357 (M+).

Example 37

2-(4-Chlorophenylsulfonyl)-3-(3-cyanophenylamino)-3-(1,2,2-trimethylpropylamino)-2-propenenitrile 1 ) 2-(4-Chlorophenylsulfonyl)-3-(3-cyanophenylamino)-3-methylsulfanyl-2-propenenitrile A solution of 4-chlorophenylsulfonylacetonitrile (1.0 g, 4.64 mmol) in dry acetone (10 ml) was stirred while dry potassium carbonate (1.28 g, 9.28 mmol) and 3-cyanophenyl isothiocyanate (0.78 g, 4.87 mmol) were added. The resulting mixture was stirred at room temperature under nitrogen for 20 h. Excess of potassium carbonate was filtered off, methyl iodide (0.859 ml, 13.9 mmol) was added to the filtrate, and stirring was continued for 3 h. The mixture was evaporated and the residue was dissolved in dichloromethane and extracted with water and brine. The organic phase was dried over magnesium sulphate, filtered and evaporated to afford 1.74 g (96%) of the title compound as golden brown crystals. Mp 168–170° C. ¹H NMR (200 MHz, CDCl$_3$): δ=2.22 (s, 3H), 7.50–7.68 (m, 6H), 7.84–7.93 (m, 2H), 9.89 (br s, 1H).

2) 2-(4-Chlorophenylsulfonyl)-3-(3-cyanophenylamino)-3-(1,2,2-trimethylpropylamino)-2-propenenitrile 2-(4-Chlorophenylsulfonyl)-3-(3-cyanophenylamino)-3-methylsulfanyl-2-propenenitrile (0.300 g, 0.6 mmol) was stirred in 2-amino-3,3-dimethylbutane (1 ml) for 48 h at 100° C. under nitrogen in a sealed flask. The reaction mixture was concentrated and the residue dissolved in dichloromethane, washed twice with 1N aqueous HCl, once with brine, and once with water. The organic phase was dried (sodium sulphate) and concentrated. The residue was triturated with ether to afford a white crystalline substance which was further purified by flash chromatography(SiO$_2$) using heptane/ethyl acetate (1:1) to yield 85 mg(25%) of the title compound. Mp 80–82 ° C. ¹H NMR (200 MHz, CDCl$_3$): δ=0.90 (s, 9H), 1.02 (d, 3H), 3.02 (m, 1H), 7.27 (s, 2H), 7.47 (d, 2H), 7.51 (d,2H), 7.81 (d, 2H);

Example 38

2-(4-Chlorophenylsulfonyl)-3-(3-cyanophenylamino)-3-cyclopentylamino-2-propenenitrile 2-(4-Chlorophenylsulfonyl)-3-(3-cyanophenylamino)-3-methylsulfanyl-2-propenenitrile(0.300 g, 0.6 mmol) was stirred in cyclopentylamine(1 ml) for 48 h at 100° C. under nitrogen in a sealed flask. Work up as described in Example 1, 2) gave 51 mg (16%) of the title compound as light brown crystals. ¹H NMR (200 MHz, CDCl$_3$): δ=1.43–1.54 (m, 4H), 1.68–1.78 (m, 4H), 3.64 (sextet, 1H), 7.07 (d, 1H), 7.21 (s, 1H), 7.40–7.55 (m, 6H), 7.77 (dd, 2H)

Example 39

2-(4-Chlorophenylsulfonyl)-3-(3-cyanophenylamino-3-(1,2-dimethylpropylamino)-2-propenenitrile 2-(4-Chlorophenylsulfonyl)-3-(3-cyanophenylamino)-3-methylsulfanyl-2-propenenitrile(0.300 g, 0.6 mmol) was stirred in cyclopentylamine(1 ml) for 48 h at 100° C. under nitrogen in a sealed flask. Work up as described in Example 37, 2) gave 44 mg (13%) of the title compound as white crystals. ¹H NMR (200 MHz, CDCl$_3$): δ=0.85 (dd, 6H), 1.01 (d, 3H), 1.67 (m, 1H), 3.13 (m,1H) 7.20–7.25 (m, 2H), 7.44–7.50 (m, 2H), 7.49 (d, 2H), 7.79 (d, 2H).

Example 40

3-(3,5-Bis(trifluoromethyl)phenylamino)-2-isopropylsulfonyl-3-(1,2,2-trimethylpropylamino)-propenenitrile 1) 3-(3,5-Bis(trifluoromethyl)phenylamino)-2-isopropylsulfonyl-3-methylsulfanyl-2-propenenitrile A solution of 2-propanesulphonylacetonitrile (4.0 g, 27.2 mmol) in dry acetone (50 ml) was stirred while dry potassium carbonate (7.52 g, 54.4 mmol) and 3,5-bis(trifluoromethyl)phenyl isothiocyanate (7.72 g, 4.87 mmol) were added. The resulting mixture was stirred at room temperature under nitrogen for 20 h. Excess of potassium carbonate was filtered off, methyl iodide (5.08 ml, 81.6 mmol) was added to the filtrate, and stirring was continued for 48 h. The mixture was evaporated and the residue was dissolved in dichloromethane and extracted with water and brine. The organic phase was dried over magnesium sulphate, filtered and evaporated to afford 11.65 g (99%) of the title compound as yellowish brown crystals. Mp 130–133° C.¹H NMR (200 MHz, CDCl$_3$): δ=1.47 (d, 6H), 2.35 (s, 3H), 3.44 (heptet, 1H), 7.73 (s, 2H), 7.80 (s, 1H), 10.10 (br s, 1H);

2) 3-(3,5-Bis(trifluoromethyl)phenylamino)-2-isopropylsulfonyl-3-(1,2,2-trimethylpropylamino)-propenenitrile 3-(3,5-Bis(trifluoromethyl)phenylamino)-2-isopropylsulfonyl-3-methylsulfanyl-2-propenenitrile (0.500 g, 0.6 mmol) was stirred in 2-amino-3,3-dimethylbutane (1 ml) for 48 h at 100° C. under nitrogen in a sealed flask. The reaction mixture was concentrated and the residue dissolved in dichloromethane, washed twice with 1N aqueous HCl, once with brine, and once with water. The organic phase was dried (sodium sulphate) and evaporated to afford 450 mg (80%) of the title compound as pale yellow crystals. Mp 177–180° C. ¹H NMR (200 MHz, CDCl$_3$): δ=0.89 (s, 9H), 1.04 (d, 3H), 1.40 (d, 6H), 2.97 (m, 1H), 3.27 (m, 1H), 7.50 (s, 2H), 7.67 (s, 1H), 9.16 (brs, 1H);

Example 41

3-(3,5-Bis(trifluoromethyl)phenylamino)-2-isopropylsulfonyl-3-cyclopentylamino-2-propenenitrile 3-(3,5-Bis(trifluoromethyl)phenylamino)-2-isopropylsulfonyl-3-methylsulfanyl-2-propenenitrile (0.500 g, 1.16 mmol) was stirred in cyclopentylamine (2 ml) for 24 h at 80° C. under nitrogen in a sealed flask. Work up as described in Example 40, 2) gave 540 mg (99%) of the title compound as white crystals. Mp 172–173 ° C. ¹H NMR (200 MHz, CDCl$_3$): δ=1.41 (d, 6H), 1.40–1.57 (m, 4H), 1.74–1.93 (m, 4H), 3.25 (heptet, 1H), 3.56 (m, 1H), 7.54 (s, 2H), 7.67 (s, 1H), 7.94 (br s, 1H), 9.22 (br s, 1H)

Example 42

3-(3,5-Bis(trifluoromethyl)phenylamino)-3-cyclobutylamino-2-isopropylsulfonyl-2-propenenitrile 3-(3,5-Bis(trifluoromethyl)phenylamino)-2-isopropylsulfonyl-3-methylsulfanyl-2-propenenitrile (0.500 g, 1.16 mmol) was stirred in cyclobutylamine (2 ml) for 24 h at 80° C. under nitrogen in a sealed flask. Work up as described in Example 40, 2) gave 470 mg (89%) of the title compound as white crystals. Mp 148–150° C. $^1$H NMR (200 MHz, CDCl$_3$): δ=1.38 (d, 6H), 1.49–1.85 (m, 2H), 2.02 (q, 4H), 3.26 (heptet, 1H), 3.53–3.77 (m, 1H), 7.46 (s, 2H), 7.64 (s, 1H), 7.96–8.14 (m, 1H), 9.17 (brs, 1H)

Example 43

3-(3,5Bis(trifluoromethyl)phenylamino)-2-isopropylsulfonyl-3-(2-methyl)propylamino)-2-propenenitrile 3-(3,5-Bis(trifluoromethyl)phenylamino)-2-isopropylsulfonyl-3-methylsulfanyl-2-propenenitrile (0.500 g, 1.16 mmol) was stirred in cyclopentylamine (2 ml) for 24 h at 80° C. under nitrogen in a sealed flask. Work up as described in Example 40, 2) gave 460 mg (87%) of the title compound as white crystals. Mp 160–163° C. $^1$H NMR (200 MHz, CDCl$_3$): δ=0.91 (d, 6H), 1.42 (d, 6H), 1.74–1.94 (m, 1H), 2.73 (t, 2H) 3.26 (heptet, 1H), 7.47 (s, 2H), 7.65 (s, 1H), 7.94–8.12 (m, 1H), 9.26 (brs 1H).

Example 44

2-Isopropylsulfonyl-3-(3-methoxyphenylamino)-3-(1,2,2-trimethylpropylamino)-2-propenenitrile 1) 2-Isopropylsulfonyl-3-(3-methoxyphenylamino)-3-methylsulfanyl-2-propenenitrile A solution of 2-propanesulfonylacetonitrile (2.0 g, 13.6 mmol) in dry acetone (25 ml) was stirred while dry potassium carbonate (1.28 g, 9.28 mmol) and 3-methoxyphenyl isothiocyanate (2.36 g, 14.3 mmol) were added. The resulting mixture was stirred at room temperature under nitrogen for 20 h. Excess of potassium carbonate was filtered off, methyl iodide (2.54 ml, 40.8 mmol) was added to the filtrate, and stirring was continued for 60 h. The mixture was evaporated and the residue was dissolved in dichloromethane and extracted with water and brine. The organic phase was dried over magnesium sulphate, filtered and evaporated to afford 4.40 g (99%) of the title compound as yellow crystals. Mp 107–110° C. $^1$H NMR (200 MHz, CDCl$_3$): δ=1.44 (d, 6H), 2.22 (s, 3H), 3.36 (heptet, 1H), 3.83 (s, 3H), 6.81 (m, 1H), 6.85 (dd, 1H), 6.87 (dd, 1H), 7.32 (dd, 1H), 9.91 (br s, 1H).

2) 2-Isopropylsulfonyl-3-(3-methoxyphenylamino)-3-(1,2,2-trimethylpropylamino)-2-propenenitrile 2-Isopropylsulfonyl-3-(3-methoxyphenylamino)-3-methylsulfanyl-2-propenenitrile(0.500 g, 1.53 mmol) was stirred in 2-amino-3,3-dimethylbutane (2 ml) for 48 h at 100° C. under nitrogen in a sealed flask. The reaction mixture was concentrated and the residue dissolved in dichloromethane,washed twice with 1N aqueous HCl, once with brine, and once with water. The organic phase was dried (sodium sulphate) and evaporated to afford 450 mg (80%) of the title compound as white crystals. Mp 59–62 ° C.$^1$H NMR (200 MHz, CDCl$_3$): δ=0.84 (s, 9H), 0.96 (d, 3H), 1.40 (d, 6H), 3.00–3.33 (m, 2H), 3.82 (s, 3H), 6.70 (dd, 1H), 6.81 (dd, 1H), 7.31 (dd, 1H), 7.73–7.94 (m, 1H) 8.95 (br s, 1H).

Example 45

3-Cyclopentylamino-2-isopropylsulfonyl-3-(3-methoxy)phenylamino-2-propenenitrile 2-Isopropylsulfonyl-3-(3-methoxyphenylamino)-3-methylsulfanyl-2-propenenitrile(0.500 g, 1.53 mmol) was stirred in cyclopentylamine (2 ml) for 48 h at 100° C. under nitrogen in a sealed flask. Work up as described in Example 44, 2) gave 490 mg (88%) of the as yellow crystals. Mp 81–85°C.$^1$H NMR (200 MHz, CDCl$_3$): δ=1.4 (d, 6H), 1.44–1.82 (m, 9H), 3.26 (sextet, 1H), 3.82 (s, 3H), 6.63 (m, 1H), 6.69 (dd, 1H), 6.77 (dd, 1H), 7.27 (dd, 1H), 8.99 (br s, 1H).

Example 46

3-Cyclobutylamino-2-isopropylsulfonylamino-3-(3-methoxy)phenylamino-2-propenenitrile 2-Isopropylsulfonyl-3-(3-methoxyphenylamino)-3-methylsulfanyl-2-propenenitrile(0.500 g, 1.53 mmol) was stirred in cyclobutylamine (2 ml) for 48 h at 100° C. under nitrogen in a sealed flask. Work up as described in Example 44, 2) gave 510 mg (95%) of the title compound as white crystals. Mp 152–155° C. $^1$H NMR (200 MHz, CDCl$_3$): δ=1.39 (d, 6H), 1.52–2.23 (m, 7H), 3.25 (hextet, 1H), 3.81 (s, 3H), 6.61 (m, 1H), 6.66 (dd, 1H), 6.77 (dd, 1H), 7.77 (dd, 1H), 7.75–8.03 (m, 1H), 8.96 (br s, 1H)

Example 47

2-Isopropylsulfonyl-3-(3-methoxy)phenylamino-3-(2-methyl)propylamino)-2-propenenitrile 2-Isopropylsulfonyl-3-(3-methoxyphenylamino)-3-methylsulfanyl-2-propenenitrile(0.500 g, 1.53 mmol) was stirred in isobutylamine (2 ml) for 48 h at 100° C. under nitrogen in a sealed flask. Work up as described in Example 44, 2) gave 410 mg (76%) of the title compound as yellow crystals. Mp 138–141° C. $^1$H NMR (200 MHz, CDCl$_3$): δ=0.87 (d, 6H), 1.39 (d, 6H), 1.66–1.85 (m, 1H), 2.69–2.90 (m, 2H), 3.25 (heptet, 1H), 3.81 (s, 3H), 6.60 (m, 1H), 6.65 (dd, 1H), 6.75 (dd, 1H), 7.26 (dd, 1H), 7.63–7.98 (m, 1H), 9.01 (br s 1H).

Example 48

3-(1,1-Dimethyl)propylamino-2-isopropylsulfonyl-3-(3-methoxy)phenylamino-2-propenenitrile 2-Isopropylsulfonyl-3-(3-methoxyphenylamino)-3-methylsulfanyl-2-propenenitrile (0.500 g, 1.53 mmol) was stirred in 1,1-dimethylpropylamine (2 ml) for 48 h at 100° C. under nitrogen in a sealed flask. Work up as described in Example 44, 2) gave 410 mg (73%) of the title compound as yellow crystals. Mp 130–134° C. $^1$H NMR (200 MHz, CDCl$_3$): δ=0.96 (t, 3H), 1.33 (s, 6H), 1.43 (d, 6H), 1.58 (q, 2H), 3.27 (heptet, 1H), 3.81 (s, 3H), 6.65 (s, 1H), 6.70 (d, 1H), 6.75 (d, 1H), 7.28 (dd, 1H).

Example 49

2-Isopropylsulfonyl-3-(3-methoxy)phenylamino-3-tert.-butylamino-2-propenenitrile 2-Isopropylsulfonyl-3-(3-methoxyphenylamino)-3-methylsulfanyl-2-propenenitrile (0.500 g, 1.53 mmol) was stirred in tert.-butylamine (2 ml) for 48 h at 100° C. under nitrogen in a sealed flask. Work up as described in Example 44, 2) gave 440 mg (82%) of the title compound as yellowish brown crystals. Mp 130–134° C.$^1$H NMR (200 MHz, CDCl$_3$): δ=1.36 (s, 9H), 1.42 (d, 6H), 3.25 (heptet, 1H), 3.79 (s, 3H), 6.67 (m, 1H), 6.71 (dd, 1H), 6.75 (dd, 1H), 7.28 (dd, 1H).

Example 50

3-(Benzo[1,3]dioxol-5-ylamino)-3-(1,1-dimethylpropylamino)-2-methanesulfonyl-2-propenenitrile 1) 3-(Benzo[1,3]dioxol-5-ylamino)-2-methanesulfonyl-3-methylsulfanyl-2-propenenitrile A solution of methanesulfonylacetonitrile (2.85 g, 23.9 mmol) in dry acetone (50 ml) was stirred while dry potassium carbonate (6.61 g, 47.8 mmol) and 3,4-methylenedioxyphenyl isothiocyanate (4.50 g, 25.1 mmol) were added. The resulting mixture was stirred at room temperature under nitrogen for 20 h. Excess of potassium carbonate was filtered off, methyl iodide (4.43 ml, 71.8 mmol) was added to the filtrate, and stirring was continued for 4 h at 50° C. The mixture was evaporated and the residue was dissolved in dichloromethane and extracted with water and brine. The organic phase was dried over magnesium sulphate, filtered and evaporated to afford 4.88 g (65%) of the title compound as golden brown crystals. Mp 168–170° C. $^1$H NMR (200 MHz, DMSO-$d_6$): δ=2.30 (s, 3H), 3.33 (s, 3H), 6.06 (s, 2H), 6.79 (dd, 1H), 6.94 (d, 1H), 6.97 (d, 1H), 9.98 (br s, 1H).

2) 3-(Benzo[1,3]dioxol-5-ylamino)-3-(1,1-dimethylpropylamino)-2-methanesulfonyl-2-propenenitrile A mixture of 3-(benzo[1,3]dioxol-5-ylamino)-2-methanesulfonyl-3-methylsulfanyl-2-propenenitrile(0.800 g, 2.5 mmol) and 1,1-dimethylpropylamine (2.92 ml) in 10 ml of acetonitrile was stirred and refluxed for one week under nitrogen. The reaction mixture was concentrated and the residue dissolved in dichloromethane, washed twice with 1N aqueous HCl, once with brine, and trice with water. The organic phase was dried (sodium sulphate) and evaporated to afford the title compound as white crystals. Mp 86–88° C. $^1$H NMR (200 MHz, DMSO-$d_6$): δ=0.90 (t, 3H), 1.34 (s, 6H), 1.70 (q, 2H), 3.04 (s, 3H), 6.66 (s, 2H), 6.66 (dd, 1H), 6.74 (d, 1H), 6.88 (d, 1H), 7.21 (s, 1H). 8.19 (s, 1H).

What is claimed is:

1. A compound selected from the group consisting of:

3-[3,5-bis(trifluoromethyl)phenylamino]-2-(4-chlorophenylsulfonyl)-3-(1,2,2-trimethylpropylamino)-2-propenenitrile, 3-[3,5-bis(trifluoromethyl)phenylamino]-2-(4-chlorophenylsulfonyl)-3-cyclopentylamino-2-propenenitrile, 3-[3,5-bis(trifluoromethyl)phenylamino]-2-(4-chlorophenylsulfonyl)-3-isopropylamino-2-propenenitrile, 3-[3,5-bis(trifluoromethyl)phenylamino]-2-(4-chlorophenylsulfonyl)-3-cyclobutylamino-2-propenenitrile, 3-[3,5-bis(trifluoromethyl)phenylamino]-2-(4-chlorophenylsulfonyl)-3-propylamino-2-propenenitrile, 2-(4-Chlorophenylsulfonyl)-3-(pyridin-3-ylamino)-3-(1,2,2-trimethylpropylamino)-2-propenenitrile, 2-(4-Chlorophenylsulfonyl)-3-(3,5-dichlorophenylamino)-3-(1,2,2-trimethylpropylamino)-2-propenenitrile, 3-(Benzo[1,3]dioxol-5-ylamino)-2-(4-chloro-phenylsulfonyl)-3-(1,2,2-trimethyl-propylamino)-propenenitrile, 3-(3,5-Bis(trifluoromethyl)phenylamino)-2-methylsulfonyl-3-(1,2,2-trimethylpropylamino)-propenenitrile, 2-(4-Chlorophenylsulfonyl)-3-(3,5-dimethoxyphenylamino)-3-(1,2,2-trimethylpropylamino)-2-propenenitrile, 3-[N-(3,5-bis(trifluoromethyl)phenyl)-N-methylamino]-2-(4-chlorophenylsulfonyl)-3-(2,2-trimethylpropylamino)-2-propenenitrile, (1'S,2'S)-3-[2-Benzyloxycyclopentylamino]-3-[3,5-bis(trifluoromethyl)phenylamino]-2-(4-chlorophenylsulfonyl)-2-propenenitrile, (1'R,2'R)-3-[2-Benzyloxycyclopentylamino]-3-[3,5-bis(trifluoromethyl)phenylamino]-2-(4-chlorophenylsulfonyl)-2-propenenitrile, (S)-3-[3,5-Bis(trifluoromethyl)phenylamino]-2-(4-chlorophenylsulfonyl)-3-(1,2,2-trimethylpropylamino)-2-propenenitrile, (S)-3-[3,5-Bis(trifluoromethyl)phenylamino]-2-(4-chlorophenylsulfonyl)-3-(1,2-dimethylpropylamino)-2-propenenitrile, (R)-3-[3,5-Bis(trifluoromethyl)phenylamino]-2-(4-chlorophenylsulfonyl)-3-(1,2-dimethylpropylamino)-2-propenenitrile, 3-[3,5-Bis(trifluoromethyl)phenylamino]-2-(4-chlorophenylsulfonyl)-3-(1,1-dimethylpropylamino)-2-propenenitrile, 3-[3,5-Bis(trifluoromethyl)phenylamino]-2-(4-chlorophenylsulfonyl)-3-(5-cyclopropyl-2-methyl-2H-pyrazol-3-ylamino)-2-propenenitrile, (R)-3-[3,5-bis(trifluoromethyl)phenylamino]-2-(4-chlorophenylsulfonyl)-3-(1,2,2-trimethylpropylamino)-2-propenenitrile, 3-(3,5-Bis(trifluoromethyl)phenylamino)-3-isopropylamino-2-methylsulfonyl-propenenitrile, (R)-3-[3,5-bis(trifluoromethyl)phenylamino]-2-methanesulfonyl-3-(1,2,2-trimethylpropylamino)-2-propenenitrile, (S)-3-[3,5-bis(trifluoromethyl)phenylamino]-2-methanesulfonyl-3-(1,2,2-trimethylpropylamino)-2-propenenitrile, 2-(4-Chlorophenylsulfonyl)-3-(3,5-dimethoxyphenylamino)-3-(1,1-dimethylpropylamino)-2-propenenitrile, 2-(4-Chlorophenylsulfonyl)-3-(3,5-dimethoxyphenylamino)-3-cyclobutylamino-2-propenenitrile, 3-(3,5-dimethoxyphenylamino)-2-methanesulfonyl-3-(1,2,2-trimethylpropylamino)-propenenitrile, 3-(3,5-dimethoxyphenylamino)-3-isopropyl-2-methanesulfonyl-propenenitrile, 3-(Benzo[1,3]dioxol-5-ylamino)-3-(1,1-dimethyl-propylamino)-2-(4-chloro-phenylsulfonyl)-propenenitrile, 3-(Benzo[1,3]dioxol-5-ylamino)-3-cyclobutylamino-2-(4-chloro-phenylsulfonyl)-propenenitile, 2-(4-Chlorophenylsulfonyl)-3-(3,5-dichlorophenylamino)-3-(1,1-dimethylpropylamino)-2-propenenitrile, 2-(4-Chlorophenylsulfonyl)-3-cyclobutylamino-3-(3,5-dichlorophenylamino)-2-propenenitrile, 3-sec-Butylamino-2-(4-chlorophenylsulfonyl)-3-(3,5-dichlorophenylamino)-2-propenenitrile, 2-Methylsulfonyl-3-(3-methoxy-5-trifluoromethyl-phenylamino)-3-(1,2,2-trimethylpropylamino)-propenenitrile, 3-(3-Fluoro-5-trifluoromethyl-phenylamino)-2-methylsulfonyl-3-(1,2,2-trimethylpropylamino)-propenenitrile, 3-(4-Chlorophenylamino)-2-methylsulfonyl-3-(1,2,2-trimethylpropylamino)-acrylonitrile, 3-(Benzothiazol-6-ylamino)-3-(1,1-dimethyl-propylamino)-2-methylsulfonyl-propenenitrile, 3-(Benzo[1,3]dioxol-5-ylamino)-2-(2,2-dimethyl-propionyl)-3-(1,1-dimethyl-propylamino)-propenenitrile, 2-(4-Chlorophenylsulfonyl)-3-(3-cyanophenylamino)-3-(1,2,2-trimethylpropylamino)-2-propenenitrile, 2-(4-Chlorophenylsulfonyl)-3-(3-cyanophenylamino)-3-cyclopentylamino-2-propenenitrile, 2-(4-Chlorophenylsulfonyl)-3-(3-cyanophenylamino-3-(1,2-dimethylpropylamino)-2-propenenitrile, 3-(3,5-Bis(trifluoromethyl)phenylamino)-2-isopropylsulfonyl-3-(1,2,2-trimethylpropylamino)-propenenitrile, 3-(3,5-Bis(trifluoromethyl)phenylamino)-2-isopropylsulfonyl-3-cyclopentylamino-2-propenenitrile, 3-(3,5-Bis(trifluoromethyl)phenylamino)-3-cyclobutylamino-2-isopropylsulfonyl-2-propenenitrile, 3-(3,5-Bis(trifluoromethyl)phenylamino)-2-isopropylsulfonyl-3-(2-methyl)propylamino-2-propenenitrile, 2-Isopropylsulfonyl-3-(3-methoxyphenylamino)-3-(1,2,2-trimethylpropylamino)-2-propenenitrile, 3-Cyclopentylamino-2-isopropylsulfonyl-3-(3-methoxy)phenylamino-2-propenenitrile, 3-Cyclobutylamino-2-isopropylsulfonylamino-3-(3-methoxy)phenylamino-2-propenenitrile, 2-Isopropylsulfonyl-3-(3-methoxy)phenylamino-3-(2-methyl)propylamino)-2-propenenitrile, 3-(1,1-Dimethyl)propylamino)-2-isopropylsulfonyl-3-(3-methoxy)phenylamino-2-propenenitrile, 2-Isopropylsulfonyl-3-(3-methoxy)phenylamino-3-tert.-butylamino-2-propenenitrile, and 3-(Benzo[1,3]dioxol-5-ylamino)-3-(1,1-dimethylpropylamino)-2-methanesulfonyl-2-propenenitrile, or a pharmaceutically acceptable salt thereof.

2. A pharmaceutical composition comprising an effective amount of a compound of claim 1, together with one or more pharmaceutically acceptable carriers or diluents.

3. The pharmaceutical composition of claim 2 in the form of an oral dosage unit or parenteral dosage unit.

4. The pharmaceutical composition of claim 2, wherein the compound is administered as a dose in a range from about 0.05 mg to 1000 mg per day.

5. The pharmaceutical composition of claim 4, wherein the compound is administered as a dose in a range from about 0.1 mg to 500 mg per day.

6. The pharmaceutical composition of claim 5, wherein the compound is administered as a dose in range from about 50 mg to 200 mg per day.

* * * * *

UNITED STATES PATENT AND TRADEMARK OFFICE
CERTIFICATE OF CORRECTION

PATENT NO.   : 6,362,205 B2
DATED        : March 26, 2002
INVENTOR(S)  : John Hansen et al.

Page 1 of 1

It is certified that error appears in the above-identified patent and that said Letters Patent is hereby corrected as shown below:

<u>Column 27,</u>
Line 60, "-3-(2,2-trimethylpropylamino)-" should read
-- -3-(1,2,2-trimethylpropylamino)- --.

Signed and Sealed this

Second Day of December, 2003

JAMES E. ROGAN
*Director of the United States Patent and Trademark Office*